(12) United States Patent
Harlev et al.

(10) Patent No.: US 10,751,134 B2
(45) Date of Patent: Aug. 25, 2020

(54) ANATOMICAL MODEL CONTROLLING

(71) Applicant: Affera, Inc., Watertown, MA (US)

(72) Inventors: Doron Harlev, Brookline, MA (US); Geoffrey Peter Wright, Boston, MA (US); Matthew Peter Neville Harwood, East Bridgewater, MA (US)

(73) Assignee: Affera, Inc., Watertown, MA (US)

( * ) Notice: Subject to any disclaimer, the term of this patent is extended or adjusted under 35 U.S.C. 154(b) by 5 days.

(21) Appl. No.: 15/593,778

(22) Filed: May 12, 2017

(65) Prior Publication Data
US 2017/0325900 A1 Nov. 16, 2017

Related U.S. Application Data

(60) Provisional application No. 62/335,120, filed on May 12, 2016, provisional application No. 62/336,143, (Continued)

(51) Int. Cl.
*A61B 34/00* (2016.01)
*G09B 23/30* (2006.01)
(Continued)

(52) U.S. Cl.
CPC .......... *A61B 34/25* (2016.02); *A61B 18/1492* (2013.01); *A61B 34/10* (2016.02); (Continued)

(58) Field of Classification Search
CPC ......... A61B 34/25; A61B 34/10; A61B 34/20; A61B 18/1492; A61B 2034/105; (Continued)

(56) References Cited

U.S. PATENT DOCUMENTS

| | | | |
|---|---|---|---|
| 4,734,690 A | 3/1988 | Waller | |
| 5,133,336 A * | 7/1992 | Savitt | A61B 1/12 600/103 |

(Continued)

FOREIGN PATENT DOCUMENTS

| | | |
|---|---|---|
| EP | 1793349 | 6/2007 |
| EP | 1837828 | 9/2007 |

(Continued)

OTHER PUBLICATIONS

"Framing (World Wide Web)", pubished by Wikipedia, [online] https://en.wikipedia.org/wiki/Framing_(World_Wide_Web) (Year: 2018).*

(Continued)

*Primary Examiner* — Tuyetlien T Tran
(74) *Attorney, Agent, or Firm* — Perkins Coie LLP

(57) ABSTRACT

Devices, systems, and methods of the present disclosure are directed to facilitating control of a graphical user interface associated with performing a medical procedure. Inputs can be received from a plurality of input devices interacting with respective sets of input options displayed on respective portions of the graphical user interface. One of the input devices can be operable by a physician, during a medical procedure, to navigate a set of input options to modify a graphical representation of at least one of a medical device and an anatomic structure displayed on the graphical user interface.

19 Claims, 10 Drawing Sheets

Related U.S. Application Data filed on May 13, 2016, provisional application No. 62/338,210, filed on May 18, 2016, provisional application No. 62/384,291, filed on Sep. 7, 2016, provisional application No. 62/410,022, filed on Oct. 19, 2016, provisional application No. 62/463,870, filed on Feb. 27, 2017.

(51) Int. Cl.
| | | |
|---|---|---|
| *A61B 34/20* | (2016.01) | |
| *A61B 18/14* | (2006.01) | |
| *A61B 34/10* | (2016.01) | |
| *G06F 3/0484* | (2013.01) | |
| *G06F 3/0481* | (2013.01) | |
| *G06F 19/00* | (2018.01) | |
| *G16H 15/00* | (2018.01) | |
| *G09B 5/02* | (2006.01) | |
| *A61B 18/00* | (2006.01) | |
| *G06F 3/02* | (2006.01) | |
| *G06F 3/0482* | (2013.01) | |

(52) U.S. Cl.
CPC .......... *A61B 34/20* (2016.02); *G06F 3/04815* (2013.01); *G06F 3/04845* (2013.01); *G06F 3/04847* (2013.01); *G06F 19/321* (2013.01); *G09B 5/02* (2013.01); *G09B 23/30* (2013.01); *G16H 15/00* (2018.01); *A61B 2018/00357* (2013.01); *A61B 2018/00577* (2013.01); *A61B 2034/105* (2016.02); *A61B 2034/2065* (2016.02); *A61B 2034/252* (2016.02); *G06F 3/0202* (2013.01); *G06F 3/0482* (2013.01)

(58) Field of Classification Search
CPC ...... A61B 2034/252; A61B 2034/2065; A61B 2018/00357; A61B 2018/00577; G16H 15/00; G06F 3/04847; G06F 3/04815; G06F 18/1492; G06F 34/20; G06F 34/10; G06F 3/04845; G06F 3/0202; G06F 3/0482; G06F 19/321; G09B 23/30; G09B 5/02
USPC .......................................... 434/256, 257, 262
See application file for complete search history.

(56) References Cited

U.S. PATENT DOCUMENTS

| | | | |
|---|---|---|---|
| 5,276,785 A | 1/1994 | Mackinlay et al. | |
| 5,364,395 A | 11/1994 | West | |
| 5,391,199 A | 2/1995 | Ben-Haim | |
| 5,433,198 A | 7/1995 | Desai | |
| 5,447,529 A | 9/1995 | Marchlinski et al. | |
| 5,623,583 A | 4/1997 | Nichino | |
| 5,655,535 A | 8/1997 | Friemel et al. | |
| 5,687,737 A | 11/1997 | Branham et al. | |
| 5,797,849 A | 8/1998 | Vesely et al. | |
| 5,820,568 A | 10/1998 | Willis | |
| 5,889,524 A | 3/1999 | Sheehan et al. | |
| 6,037,937 A * | 3/2000 | Beaton ................. | G06F 3/0485 715/764 |
| 6,120,435 A * | 9/2000 | Eino ................. | A61B 1/00039 348/65 |
| 6,175,655 B1 | 1/2001 | George, III et al. | |
| 6,216,027 B1 | 4/2001 | Willis | |
| 6,256,038 B1 | 7/2001 | Krishnamurthy | |
| 6,271,856 B1 | 8/2001 | Krishnamurthy | |
| 6,304,267 B1 | 10/2001 | Sata | |
| 6,377,865 B1 | 4/2002 | Edelsbrunner et al. | |
| 6,443,894 B1 | 9/2002 | Sumanaweera et al. | |
| 6,556,206 B1 | 4/2003 | Benson et al. | |
| 6,664,986 B1 | 12/2003 | Kopelman et al. | |
| 6,961,911 B2 | 11/2005 | Suzuki | |
| 6,968,299 B1 | 11/2005 | Bernardini et al. | |
| 7,023,432 B2 | 4/2006 | Fletcher et al. | |
| 7,092,773 B1 | 8/2006 | Oliver et al. | |
| 7,155,042 B1 | 12/2006 | Cowan | |
| 7,285,117 B2 | 10/2007 | Krueger | |
| 7,315,638 B2 | 1/2008 | Hara | |
| 7,365,745 B2 | 4/2008 | Olson | |
| 7,450,749 B2 | 11/2008 | Rouet et al. | |
| 7,656,418 B2 | 2/2010 | Watkins et al. | |
| 7,714,856 B2 | 5/2010 | Waldinger et al. | |
| 7,894,663 B2 | 2/2011 | Berg et al. | |
| 8,014,561 B2 | 9/2011 | Farag et al. | |
| 8,334,867 B1 | 12/2012 | Davidson | |
| 8,636,729 B2 | 1/2014 | Brady et al. | |
| 8,784,413 B2 | 7/2014 | Schwartz | |
| 8,786,594 B2 | 7/2014 | Kushwaha et al. | |
| 8,817,076 B2 | 8/2014 | Steen | |
| 8,920,368 B2 | 12/2014 | Sandhu et al. | |
| 9,211,160 B2 | 12/2015 | Pivotto et al. | |
| 9,245,382 B2 | 1/2016 | Zhou et al. | |
| 9,256,980 B2 | 2/2016 | Kirk | |
| 9,311,744 B2 | 4/2016 | Wu et al. | |
| 9,358,076 B2 * | 6/2016 | Moll ................. | A61B 5/0084 |
| 9,439,736 B2 | 9/2016 | Olson | |
| 9,613,291 B2 | 4/2017 | Wu et al. | |
| 9,888,973 B2 | 2/2018 | Olson et al. | |
| 10,163,252 B2 | 12/2018 | Harlev | |
| 10,376,320 B2 | 8/2019 | Harlev | |
| 2002/0062083 A1 * | 5/2002 | Ohara ................. | A61B 1/00082 600/462 |
| 2002/0062084 A1 * | 5/2002 | Ohara ................. | A61B 1/00082 600/462 |
| 2002/0165541 A1 | 11/2002 | Whitman | |
| 2003/0032862 A1 * | 2/2003 | Ota ................. | A61B 1/00068 600/158 |
| 2003/0060831 A1 * | 3/2003 | Bonutti ................. | A41D 19/0157 606/86 R |
| 2003/0176778 A1 | 9/2003 | Messing | |
| 2003/0189567 A1 | 10/2003 | Baumberg | |
| 2003/0229282 A1 | 12/2003 | Burdette et al. | |
| 2004/0043368 A1 | 3/2004 | Hsieh | |
| 2004/0249809 A1 | 12/2004 | Ramani | |
| 2005/0128184 A1 * | 6/2005 | McGreevy ......... | A61B 18/1206 345/156 |
| 2006/0159323 A1 | 7/2006 | Sun | |
| 2006/0203089 A1 * | 9/2006 | Akimoto ............ | A61B 1/00009 348/113 |
| 2006/0241445 A1 | 10/2006 | Altmann et al. | |
| 2007/0208260 A1 | 9/2007 | Afonso | |
| 2007/0220444 A1 * | 9/2007 | Sunday ................. | G06F 3/0488 715/788 |
| 2007/0299351 A1 * | 12/2007 | Harlev ................. | A61B 5/0422 600/509 |
| 2007/0299352 A1 * | 12/2007 | Harlev ................. | A61B 5/0422 600/509 |
| 2007/0299353 A1 * | 12/2007 | Harlev ................. | A61B 5/0422 600/509 |
| 2008/0138009 A1 | 6/2008 | Block et al. | |
| 2008/0161681 A1 * | 7/2008 | Hauck ................. | A61B 5/06 600/424 |
| 2008/0221425 A1 * | 9/2008 | Olson ................. | A61B 90/36 600/407 |
| 2008/0221438 A1 * | 9/2008 | Chen ................. | A61B 5/0422 600/424 |
| 2008/0270095 A1 | 10/2008 | Lombaert et al. | |
| 2008/0308256 A1 | 12/2008 | Deborski | |
| 2009/0076476 A1 | 3/2009 | Barbagli et al. | |
| 2009/0163810 A1 * | 6/2009 | Kanade ................. | A61B 5/06 600/443 |
| 2009/0171274 A1 * | 7/2009 | Harlev ................. | A61B 5/0422 604/95.04 |
| 2009/0177111 A1 * | 7/2009 | Miller ................. | A61B 5/053 600/547 |
| 2009/0264741 A1 | 10/2009 | Markowitz | |
| 2009/0264742 A1 | 10/2009 | Markowitz | |
| 2009/0281418 A1 | 11/2009 | Ruijters et al. | |
| 2010/0053208 A1 | 3/2010 | Menningen et al. | |

(56) References Cited

U.S. PATENT DOCUMENTS

| | | | |
|---|---|---|---|
| 2010/0100081 A1* | 4/2010 | Tuma | A61B 34/20 |
| | | | 606/1 |
| 2010/0106009 A1* | 4/2010 | Harlev | A61B 5/053 |
| | | | 600/424 |
| 2010/0168560 A1* | 7/2010 | Hauck | A61B 5/06 |
| | | | 600/424 |
| 2010/0256558 A1* | 10/2010 | Olson | A61B 34/20 |
| | | | 604/95.01 |
| 2010/0259542 A1 | 10/2010 | Visser et al. | |
| 2010/0305427 A1* | 12/2010 | Huber | A61B 34/20 |
| | | | 600/424 |
| 2010/0317981 A1 | 12/2010 | Grunwald | |
| 2011/0034971 A1* | 2/2011 | Svanberg | A61N 5/0601 |
| | | | 607/88 |
| 2011/0060762 A1 | 3/2011 | Bessette | |
| 2011/0112569 A1* | 5/2011 | Friedman | A61B 5/042 |
| | | | 606/205 |
| 2011/0144806 A1* | 6/2011 | Sandhu | A61B 34/71 |
| | | | 700/264 |
| 2011/0152684 A1 | 6/2011 | Altmann et al. | |
| 2011/0175990 A1* | 7/2011 | Sato | H04N 7/183 |
| | | | 348/65 |
| 2011/0236868 A1 | 9/2011 | Bronstein | |
| 2011/0243323 A1* | 10/2011 | Sato | A61B 1/00009 |
| | | | 380/200 |
| 2012/0004540 A1* | 1/2012 | Liu | A61B 5/06 |
| | | | 600/424 |
| 2012/0089038 A1* | 4/2012 | Ryu | A61B 5/046 |
| | | | 600/515 |
| 2012/0097178 A1 | 4/2012 | Helm et al. | |
| 2012/0123404 A1 | 5/2012 | Craig | |
| 2012/0169857 A1* | 7/2012 | Sato | G06F 19/321 |
| | | | 348/65 |
| 2012/0174022 A1 | 7/2012 | Sandhu et al. | |
| 2012/0177269 A1 | 7/2012 | Lu et al. | |
| 2012/0221569 A1* | 8/2012 | Sato | G06F 17/30115 |
| | | | 707/736 |
| 2012/0245465 A1 | 9/2012 | Hansegard et al. | |
| 2013/0002968 A1* | 1/2013 | Bridge | H04N 19/97 |
| | | | 348/744 |
| 2013/0030285 A1* | 1/2013 | Vaillant | A61B 6/12 |
| | | | 600/424 |
| 2013/0033519 A1* | 2/2013 | Sato | G06F 3/0482 |
| | | | 345/619 |
| 2013/0129170 A1 | 5/2013 | Zheng | |
| 2013/0241929 A1 | 9/2013 | Massaeawa et al. | |
| 2013/0286012 A1 | 10/2013 | Medioni | |
| 2014/0100453 A1 | 4/2014 | Kemp | |
| 2014/0328524 A1 | 11/2014 | Calabrese | |
| 2015/0018698 A1 | 1/2015 | Safran | |
| 2015/0042657 A1 | 2/2015 | Smith-Casem | |
| 2015/0057529 A1* | 2/2015 | Merschon | A61B 5/061 |
| | | | 600/424 |
| 2015/0119735 A1* | 4/2015 | Yang | A61B 5/04012 |
| | | | 600/509 |
| 2015/0324114 A1 | 11/2015 | Hurley et al. | |
| 2016/0000300 A1* | 1/2016 | Williams | A61B 1/00016 |
| | | | 600/109 |
| 2016/0147308 A1 | 5/2016 | Gelman | |
| 2016/0196666 A1 | 7/2016 | Venkatraghavan et al. | |
| 2016/0242855 A1 | 8/2016 | Fichtinger et al. | |
| 2016/0275653 A1 | 9/2016 | Ross | |
| 2016/0364862 A1 | 12/2016 | Reicher et al. | |
| 2016/0367168 A1 | 12/2016 | Malinin et al. | |
| 2017/0038951 A1 | 2/2017 | Reicher et al. | |
| 2017/0065256 A1 | 3/2017 | Kim et al. | |
| 2017/0202469 A1 | 7/2017 | Scharf et al. | |
| 2017/0209072 A1* | 7/2017 | Oren | A61B 5/062 |
| 2017/0245936 A1 | 8/2017 | Kanade et al. | |
| 2017/0265943 A1* | 9/2017 | Sela | G06F 19/00 |
| 2017/0301124 A1 | 10/2017 | Dala-Krishna | |
| 2017/0323473 A1 | 11/2017 | Wright | |
| 2017/0325901 A1 | 11/2017 | Harlev et al. | |
| 2017/0330487 A1 | 11/2017 | Harlev | |
| 2018/0228386 A1* | 8/2018 | McCall | A61B 5/7435 |
| 2018/0289435 A1* | 10/2018 | Namiki | A61B 34/25 |
| 2019/0004621 A1* | 1/2019 | Nuber | G06F 3/038 |
| 2019/0096122 A1 | 3/2019 | Harlev | |

FOREIGN PATENT DOCUMENTS

| | | |
|---|---|---|
| EP | 2332461 | 6/2011 |
| WO | WO-03039350 | 5/2003 |
| WO | 2005022468 | 3/2005 |
| WO | 2005063125 | 7/2005 |
| WO | WO-2008107905 | 9/2008 |
| WO | 2010054409 | 5/2010 |
| WO | 2017192746 | 11/2017 |
| WO | 2017192781 | 11/2017 |
| WO | 2017197114 | 11/2017 |
| WO | WO-2017197294 | 11/2017 |

OTHER PUBLICATIONS

ISA, "PCT Application No. PCT/US17/32378 International Search Report and Written Opinion dated Dec. 20, 2017", 17 pages.

ISA, "PCT Application No. PCT/US17/32378 Invitation to Pay Additional Fees and Partial Search Report dated Oct. 23, 2017", 15 pages.

ISA, "PCT Application No. PCT/US17/32459 International Search Report and Written Opinion dated Jul. 21, 2017", 11 pages.

3D-Doctor User's Manual: 3D Imaging, Modeling and Measurement Software (2012) (pp. 1-269) ("3D Doctor").

Bernardini, Fausto et al., "The Ball-Pivoting Algorithm for Surface Reconstruction", IEEE transactions on visualization and computer graphics 5.4 (1999), Oct. 1999, pp. 349-359.

Carr, J.C. et al., "Reconstruction and Representation of 3D Objects with Radial Basis Functions", Proceedings of the 28th annual conference on Computer graphics and interactive techniques. ACM, 2001, 10 Pages.

Chen, Yang et al., "Description of Complex Objects from Multiple Range Images Using an Inflating Balloon Model", Computer Vision and Image Understanding 61.3, May 1995, pp. 325-334.

Curless, Brian et al., "A Volumetric Method for Building Complex Models from Range Images", Proceedings of the 23rd annual conference on Computer graphics and interactive techniques. ACM, 1996, 10 Pages.

Davis, James et al., "Filling holes in complex surfaces using volumetric diffusion", 3D Data Processing Visualization and Transmission, 2002. Proceedings. First International Symposium on. IEEE, 2002, 15 Pages.

Elfes, Alberto, "Using Occupancy Grids for Mobile Robot Perception and Navigation", Computer, vol. 22, Issue: 6, Jun. 1989, pp. 46-57.

Gelas, Arnaud et al., "Surface Meshes Smoothing", Insight Journal. Feb. 20, 2009, 6 Pages.

Hilbert, Sebastian et al., "Real-Time Magnetic Resonance-guided ablation of typical right atrial flutter using a combination of active catheter tracking and passive catheter visualization in main: initial results from a consecutive patient series", Aug. 27, 2015, 6 pages.

International Search Report and Written Opinion dated Jul. 14, 2017; International Patent Application No. PCT/US2017/030877; 9 pages.

International Search Report and Written Opinion dated Jul. 25, 2017; International Patent Application No. PCT/US2017/030928; 12 pages.

International Search Report and Written Opinion dated Feb. 1, 2019; International Patent Application No. PCTUS2018/048460; 19 pages.

Kazhdan, Michael et al., "Poisson Surface Reconstruction", Eurographics Symposium on Geometry Processing, 2006, 10 Pages.

Lempitsky, Victor, "Surface Extraction from Binary Volumes with Higher-Order Smoothness", Computer Vision and Pattern Recognition (CVPR), 2010 IEEE Conference on. IEEE, Jun. 2010, 6 Pages.

(56) References Cited

OTHER PUBLICATIONS

Liang, Jian et al., "Robust and Efficient Implicit Surface Reconstruction for Point Clouds Based on Convexified Image Segmentation", Journal of Scientific Computing 54.2-3, 2013, pp. 577-602.

Lounsbery, Michael et al., "Parametric Surface Interpolation", IEEE Computer Graphics and Applications 12.5 (1992) Sep. 1992, pp. 45-52.

Schroeder, William et al., "Flying Edges: A High-Performance Scalable Isocontouring Algorithm", IEEE Xplore, Oct. 2015, 8 pages.

Wang, Jianning et al., "A Hole-Filling Strategy for Reconstruction of Smooth Surfaces in Range Images", Computer Graphics and Image Processing, 2003. SIBGRAPI 2003. XVI Brazilian Symposium on. IEEE, Oct. 2003, 8 pages.

Zhao, Hong-Kai et al., "Fast Surface Reconstruction Using the Level Set Method", Variational and Level Set Methods in Computer Vision, 2001. Proceedings. IEEE Workshop on. IEEE, Jul. 2001, 8 pages.

Sethian, J.A., "Level Set Methods and Fast Marching Methods", Cambridge University Press, 1999, 21 Pages.

ISA, "PCT Application No. PCT/US17/32160 International Search Report and Written Opinion dated Aug. 21, 2017", 10 pages.

\* cited by examiner

ANATOMICAL MODEL CONTROLLING

CROSS-REFERENCE TO RELATED APPLICATIONS

This application claims the benefit under 35 U.S.C. § 119(e) of U.S. Prov. App. No. 62/335,120, filed May 12, 2016, U.S. Prov. App. No. 62/336,143, filed May 13, 2016, U.S. Prov. App. No. 62/338,210, filed May 18, 2016, U.S. Prov. App. No. 62/384,291, filed Sep. 7, 2016, U.S. Prov. App. No. 62/410,022, filed Oct. 19, 2016, and U.S. Prov. App. No. 62/463,870, filed Feb. 27, 2017, with the entire contents of each of these applications hereby incorporated herein by reference.

This application is also related to commonly-owned U.S. patent application Ser. No. 15/594,039, filed on even date herewith and entitled "THREE-DIMENSIONAL CARDIAC REPRESENTATION," the entire contents of which are hereby incorporated herein by reference.

BACKGROUND

Three-dimensional models are sometimes used to assist in the placement or use of a device when such placement or use is not easily observable or practical. For example, in medical procedures, three-dimensional models presented on a graphical user interface are used to assist in the placement and use of medical devices as part of diagnosis or treatment of patients. An example of such a medical procedure carried out with the assistance of a three-dimensional model presented on a graphical user interface is the use of a catheter for radio frequency ("RF") ablation to terminate certain arrhythmias in the heart.

SUMMARY

Devices, systems, and methods of the present disclosure facilitate control of a graphical user interface by a physician during a medical procedure, such as a procedure in which the physician is maneuvering a catheter in a hollow anatomic structure (e.g., a heart cavity). For example, using the devices, systems, and methods of the present disclosure, a variety of options related to the medical procedure can be presented to the physician during the medical procedure by presenting subsets of actions to the physician on the graphical user interface on a state-dependent basis, with the state at any given time depending on the context of the action being performed by the physician at the given time. The presentation of subsets of actions to the physician on a state-dependent basis can, for example, facilitate control of the graphical user interface by the physician using an input device with only a few input sources (e.g., buttons).

As compared to an interface requiring a keyboard and a mouse, the simplified input interface associated with the devices, systems, and methods of the present disclosure can improve the ability of the physician to manipulate the graphical user interface, of a graphical representation of the hollow anatomic structure, or both while the physician is also manipulating the catheter. Additionally, or alternatively, the devices, systems, and methods of the present disclosure can facilitate control of the graphical user interface and/or the graphical representation of the hollow anatomic structure from within the sterile field and, optionally, without the assistance of a person outside of the sterile field. Such autonomy of control by the physician can, for example, simplify medical procedures by reducing, or even eliminating, the need for the physician to communicate with a person outside of the sterile field to achieve desired control over the graphical user interface and, further or instead, control over the graphical representation of the hollow anatomic structure.

According to one aspect, a method includes receiving a signal indicative of location of a cardiac catheter in a cavity of a patient's heart, displaying, on a first portion of a graphical user interface, a graphical representation of the cavity of the patient's heart, the graphical representation based on the received location signal from the cardiac catheter, receiving, from a first input device, a first input command based on a first set of input options displayed on the first portion of the graphical user interface, receiving, from a second input device, a second input command based on a second set of input options displayed on a second portion of the graphical user interface, and, based on the first input command and the second input command, modifying the graphical representation in the first portion of the graphical user interface.

In certain implementations, modifying the graphical representation can include adjusting the displayed graphical representation according to an order in which the first input command and the second input command are received.

In some implementations, at least some of the second set of input options can be the same as some of the first set of input options.

In certain implementations, receiving the first input command can include receiving the first input command along a first communication channel and receiving the second input command can include receiving the second input command along a second communication channel, each communication channel dedicated to the respective portion of the graphical user interface.

In some implementations, the method can further include receiving navigation commands for moving, within the second portion of the graphical user interface, between the options in the second set of input options. For example, the second set of input options represented on the second portion of the graphical user interface can correspond to a current state of a state machine having a plurality of states. In certain instances, the second input command or at least one of the navigation commands can change a current state of a state machine. Additionally, or alternatively, in each of the plurality of states, the second input command or at least one of the navigation commands can change a top-level state of the current state of the state machine. For example, the navigation commands can include commands to change the top-level state of the current state of the state machine between a build state, a view state, and a tag state.

In certain implementations, when the current state is the build state, representing the current state in the second portion of the graphical user interface can include representing input command options to start and to stop building a three-dimensional representation, shown in the first portion of the graphical user interface, of the cavity of the patient's heart. Additionally, or alternatively, when the current state is the view state, representing the current state in the second portion of the graphical user interface includes representing options to turn an automatic view control on and off. Further, or instead, when the current state is the tag state, representing the current state in the second portion of the graphical user interface can include a selection of identifiers corresponding to anatomic features of the heart cavity.

In some implementations, the navigation commands can include discrete direction commands. For example, the discrete direction commands can include commands for left, right, up, and down navigation in the second portion of the graphical user interface.

In certain implementations, at least one of the navigation commands can scroll through the second set of options displayed as an infinite wheel.

In some implementations, the method can further include detecting receipt of an initial command, the initial command being one of the second input command or one of the navigation commands, and, based on the detected receipt of the initial command, changing one or more display features of the second portion of the graphical user interface. For example, changing the one or more display features of the second portion of the graphical user interface can include displaying, in the second portion of the graphical user interface, additional input options of the second set of input options. Additionally, or alternatively, changing one or more display features of the second portion of the graphical user interface can include changing the one or more display features of the second portion, relative to the first portion of the graphical user interface, between a baseline configuration and modified configuration. By way of example, changing the one or more display features of the second portion of the graphical user interface relative to the first portion of the graphical user interface between a baseline configuration and a modified configuration can include changing a size of the second portion of the graphical user interface relative to a size of the first portion of the graphical user interface. Also, or instead, changing the one or more display features of the second portion of the graphical user interface relative to the first portion of the graphical user interface can include changing an opacity of the second portion of the graphical user interface relative to an opacity of the first portion of the graphical user interface. By way of further or alternative example, changing the one or more display features of the second portion of the graphical user interface relative to the first portion of the graphical user interface can include changing a position of the second portion of the graphical user interface relative to a position of the first portion of the graphical user interface. As still a further or alternative example, changing the one or more display features of the second portion of the graphical user interface relative to the first portion of the graphical user interface between the baseline configuration and the modified configuration can include changing the second portion of the graphical user interface from the modified configuration to the baseline configuration if a time between receipt of a first one of the input commands and receipt of a second one of the input commands exceeds a predetermined inactivity threshold period. Additionally, or alternatively, changing the one or more display features of the second portion of the graphical user interface relative to the first portion of the graphical user interface between the baseline configuration and the modified configuration can include changing the second portion of the graphical user interface from the modified configuration to the baseline configuration based on a received input command of the second set of input commands.

In certain implementations, the first portion can be viewable on the graphical user interface at the same time that the second portion can be viewable on the graphical user interface. In some instances, modification of the displayed graphical representation can include adjusting an orientation of a displayed view of the graphical representation of the heart cavity of the patient. For example, adjusting the orientation of the displayed view of the graphical representation of the heart cavity of the patient can include rotating the graphical representation of the heart cavity about an axis.

In some implementations, modifying the displayed graphical representation in the first portion of the graphical user interface can include modifying a pose of the graphical representation in the first portion of the graphical user interface.

In certain implementations, the second input command can include a discrete selection command.

In some implementations, receiving the second input command can include receiving a wireless input command.

In certain implementations, the second input device can be a remote device and receiving the second input command can include receiving an input command from the remote device.

In some implementations, the second input device can be releasably coupled to a handle of the cardiac catheter.

According to another aspect, a method includes receiving as signal indicative of a location of a catheter tip in a cavity of a patient's heart, displaying, on a graphical user interface, a graphical representation of the location of the catheter tip in the cavity of the patient's heart, receiving, from a first input device, a first input command responsive to a first set of input options displayed on the graphical user interface, receiving, from a second input device separate from the first input device, navigation commands and a second input command, the navigation commands for moving through a second set of input options, and the second input command responsive to the second set of input options displayed on the graphical user interface, and based on the first input command and the second input command, modifying the displayed graphical representation.

In some implementations, modifying the graphical representation can include modifying the graphical representation according to an order in which the first input command and the second input command are received.

In certain implementations, the method can further include displaying the first set of input options on a first portion of the graphical user interface, and displaying the second set of input options on a second portion of the graphical user interface.

In some implementations, the second set of input options can include available transitions of a state machine. Additionally, or alternatively, the second set of input options displayed on the graphical user interface are based on a current state of the state machine.

In certain implementations, receiving the navigation commands can include receiving discrete directional commands for moving through the second set of input options. For example, the discrete directional commands can correspond to right, left, up, and down navigation through the second set of input options.

In certain implementations, receiving the navigation commands can include receiving an analog command for navigating through the second set of input options.

In some implementations, the second set of input options can be arranged in an infinite wheel and receiving the navigation commands can include receiving a scroll command for moving through states of the infinite wheel.

In certain implementations, the method can further include modifying, based on the received navigation commands, one or more display features of the second set of input options between a baseline configuration and a modified configuration. For example, a size of the displayed second set of input options to relative to a size of the displayed first set of input options can be greater in the modified configuration than in the baseline configuration.

Additionally, or alternatively, an opacity of the displayed second set of input options relative to an opacity of the first set of input options can be greater in the modified configuration than in the baseline configuration. Further, or instead, a position of the second set of input options relative to the first set of input options on the graphical user interface can be different in the modified configuration than in the baseline configuration.

In some implementations, modifying the one or more display features of the second set of input options between a baseline configuration and a modified configuration can include changing the second set of input options from the modified configuration to the baseline configuration if a time between receipt of a first input command and receipt of a second input command exceeds a predetermined inactivity threshold period.

In certain implementations, modifying the one or more display features of the second set of input options between a baseline configuration and a modified configuration can include changing the second set of input options from the baseline configuration to the modified configuration if an input command of the second set of input options is received.

According to still another aspect, a non-transitory, computer-readable storage medium has stored thereon computer executable instructions for causing one or more processors to perform operations including receiving a signal indicative of a location of a catheter tip in a cavity of a patient's heart, displaying, on a graphical user interface, a graphical representation of the location of the catheter tip in the cavity of the patient's heart, receiving, from a first input device, a first input command responsive to a first set of input options displayed on the graphical user interface, receiving, from a second input device separate from the first input device, navigation commands and a second input command, the navigation commands for moving through a second set of input options, and the second input command responsive to the second set of input options displayed on the graphical user interface, and, based on the first input command and the second input command, modifying the graphical representation on the graphical user interface.

In some implementations, the operations can further include displaying the first set of input options on a first portion of the graphical user interface, and displaying the second set of input options on a second portion of the graphical user interface.

In certain implementations, receiving the navigation commands can include receiving an analog command for navigating through the second set of input options.

In some implementations, the operations can further include modifying, based on the received navigation commands, one or more display features of the second set of input options between a baseline configuration to a modified configuration.

According to still another aspect, a catheter includes a catheter shaft having a proximal end region and a distal end region, a handle portion coupled to the proximal end region of the catheter shaft, an articulation controller supported on the handle portion, the articulation controller in mechanical communication with the catheter shaft to modify a position of the distal end region of the catheter shaft, and a graphical user interface (GUI) controller coupled to the handle portion and disposed relative to the articulation controller along the handle portion such that a user can maintain the distal end region of the catheter in place while manipulating the GUI controller.

In certain implementations, the GUI controller can be configured for communication with a graphical representation of at least a portion of the catheter on a GUI.

In some implementations, the GUI controller can be disposed relative to the articulation controller along the handle portion such that the user can manipulate the GUI controller and the articulation controller through one-handed operation.

In certain implementations, the GUI controller can be disposed relative to the articulation controller along the handle portion such that the user can manipulate the GUI controller and the articulation controller using the same grip of the handle portion.

In some implementations, the GUI controller can be releasably coupled to the handle portion.

In some implementations, the GUI controller can be rotatably coupled to the handle portion such that the GUI controller is rotatable about an axis defined by the catheter shaft. For example, the GUI controller can be rotatable about 180 degrees of a circumference of the catheter shaft. Additionally, or alternatively, the GUI controller can be freely rotatable about a circumference of the catheter shaft.

In certain implementations, the GUI controller can include discrete navigation inputs. For example, the navigation inputs can include right, left, up, and down navigation inputs.

In some implementations, the GUI controller can include a capacitive touch portion.

In certain implementations, the GUI controller can be coupled to the handle portion distal to the articulation controller.

In some implementations, the GUI controller can include one or more inputs and the articulation controller can be moveable along a plane substantially perpendicular to a direction of movement of the one or more inputs.

In certain implementations, the GUI controller can include an orientation feature extending from a surface of the GUI controller to provide tactile feedback to the user regarding a position of the user's hand with respect to the GUI controller.

In some implementations, the GUI controller is sterilizable. For example, the GUI controller can be formed of components compatible with one or more of the following sterilization techniques: ethylene oxide sterilization, autoclave sterilization, gamma radiation, gas-plasma sterilization.

In certain implementations, the catheter can further include at least one electrode mechanically coupled to the distal end region of the catheter shaft. For example, the at least one electrode can be disposed along an expandable element coupled to the distal end region of the catheter shaft.

In some implementations, the GUI controller can be configured for communication with a remote graphical user interface. For example, the GUI controller can include a transmitter. Additionally, or alternatively, the GUI controller includes a wireless transmitter.

According to another aspect, a system includes a graphical user interface, one or more processors, a first input device in communication with the one or more processors, a second input device separate from the first input device, the second input device in communication with the one or more processors, and a non-transitory, computer-readable storage medium having stored thereon computer executable instructions for causing one or more processors to perform operations including receiving a signal indicative of a location of a catheter tip in a cavity of a patient's heart, displaying, on the graphical user interface, a graphical representation of the cavity of the patient's heart, receiving, from the first input device, a first input command responsive to a first set of input options displayed on the graphical user interface, receiving, from the second input device separate from the first input device, navigation commands and a second input command, the navigation commands for moving through a second set of input options, and the second input command responsive to the second set of input options displayed on the graphical user interface, and, based on the first input command and the second input command, modifying the displayed graphical representation.

According to still another aspect, a remote communication device includes a user interface including one or more inputs, a transmitter in communication with the user interface to send one or more control commands to a remote processor, and a housing carrying the user interface and the transmitter, the housing securable to an outer circumference of a catheter shaft with the user interface at least partially constrained in at least one direction relative to the catheter shaft.

In certain implementations, the transmitter includes a wireless transmitter.

In some implementations, with the housing secured to the outer circumference of the catheter shaft, the user interface can be at least partially constrained in a radial direction relative to the catheter shaft. Additionally, or alternatively, with the housing secured to the outer circumference of the catheter shaft, the user interface can be movable less than about 1 cm in the radial direction relative to the catheter shaft. Further, or instead, with the housing secured to the outer circumference of the catheter shaft, the user interface can be entirely constrained in the radial direction relative to the catheter shaft. Still further, or instead, with the housing secured to the outer circumference of the catheter shaft, the one or more inputs of the user interface can be depressible in a direction parallel to the at least one partially constrained direction of the user interface.

In certain implementations, with the housing secured to the outer circumference of the catheter shaft, the user interface can be movable along an axis defined by the catheter shaft.

In some implementations, with the housing secured to the outer circumference of the catheter shaft, the user interface can be rotatable about the catheter shaft.

In certain implementations, with the housing secured to the outer circumference of the catheter shaft, the user interface can be rotatable about an axis of rotation coaxial with an axis defined by the catheter shaft. For example, the user interface can be rotatable 360 degrees about the catheter shaft. Additionally, or alternatively, the one or more inputs can be depressible in a direction transverse to the axis of rotation of the user interface.

In some implementations, with the housing secured to the outer circumference of the catheter shaft, the user interface can be rotatable relative to a handle coupled to the catheter shaft.

In certain implementations, the housing can define a recess positionable about at least a portion of the outer circumference of the catheter shaft. For example, the portion of the housing defining the recess can include a first section and a second section releasably engageable with the first section to define the recess. For example, the second section can be releasably engageable with the first section through an interference fit. Additionally, or alternatively, the first section of the housing can include a first material, the second section of the housing can include a second material magnetically attracted to the first material, and the first section and the second section of the housing can be releasably engageable to one another through a magnetic force between the first material and the second material. Further, or instead, the first section and the second section can each define a portion of the recess. By way of example, the first section and the second section can each define substantially half of the recess. As a further or alternative example, the portion of the housing defining the recess can further include a hinge disposed between the first section and the second section, the hinge pivotable to move the first section and the second section into releasable engagement with one another.

In some implementations, the housing can include a clip positionable about at least a portion of the outer circumference of the catheter shaft.

In certain implementations, the housing can be securable in a fixed axial position relative to the catheter shaft. For example, the housing can be securable in the fixed axial position relative to the catheter shaft through an interference fit between the outer circumference of the catheter shaft and the housing.

In some implementations, the one or more inputs can include a capacitive touch portion.

In certain implementations, the housing can be formed of material compatible with sterilization.

In some implementations, the remote communication device can further include a cover enclosing the housing and the user interface, the cover removable from the housing and the user interface, and the cover formed of material compatible with one or more of the following sterilization techniques: ethylene oxide sterilization, autoclave sterilization, gamma radiation, gas-plasma sterilization.

In certain implementations, the housing can define a volume and the transmitter is disposed within the volume. For example, the one or more inputs can be at least partially disposed outside of the volume. By way of further or alternative example, the volume can be substantially resistant to fluid ingress.

In some implementations, the remote communication device can further include a power source in communication with the transmitter, the power source carried by the housing. The power source can be, for example, releasably coupled to the housing.

In certain implementations, the remote communication device can further include a processor carried by the housing, the processor in communication with the user interface and the transmitter.

According to still another aspect, a method includes positioning a remote communication device about shaft of a catheter, the shaft having a proximal end region coupled to a handle and a distal end region coupled to an electrode, and securing the remote communication device to an outer circumference of the shaft, along the proximal end region of the shaft, the remote communication device including a housing, a user interface, a transmitter (e.g., a wireless transmitter) in electrical communication with the user interface to send one or more control commands to a remote processor, the housing carrying the user interface and the transmitter, wherein the user interface includes one or more inputs and, with the remote communication device secured to the outer circumference of the shaft, the user interface is at least partially constrained in at least one direction relative to the shaft.

In some implementations, the remote communication device can be secured to the outer circumference of the shaft, the user interface can be at least partially constrained in a radial direction relative to the shaft. For example, with the remote communication device secured to the outer circumference of the shaft, the user interface can be movable less than about 1 cm in the radial direction relative to the shaft. Further, or instead, with the remote communication device secured to the outer circumference of the shaft, the user interface can be entirely constrained in the radial direction relative to the shaft.

In certain implementations, with the remote communication device secured to the outer circumference of the catheter shaft, the one or more inputs of the user interface can be depressible in a direction parallel to the at least one partially constrained direction of the user interface.

In some implementations, with the remote communication device secured to the outer circumference of the catheter shaft, the user interface can be movable along an axis defined by the shaft.

In certain implementations, the user interface can be rotatable about an axis of rotation coaxial with an axis defined by the shaft. For example, the user interface can be rotatable 360 degrees about the axis of rotation.

In certain implementations, the one or more inputs can be depressible in a direction transverse to the axis of rotation of the user interface.

In some implementations, the user interface can be rotatable relative to the handle coupled to the shaft.

In certain implementations, the housing can define a recess, and securing the remote communication device to the proximal end region of the shaft can include positioning the recess about at least a portion of the outer circumference of the shaft. For example, the portion of the housing defining the recess can include a first section and a second section, and securing the remote communication device to the proximal end region of the shaft can include coupling the first section and the second section to one another about the proximal end region of the shaft.

In some implementations, the housing can be secured to the proximal end region of the shaft with the housing extending distal to the handle. For example, the housing can be secured to the proximal end region of the shaft such that the housing is adjacent to the handle. As a more specific example, the housing can be mechanically coupled to the handle.

In certain implementations, the method can further include pressing the one or more inputs to generate one or more control commands based on the one or more inputs. Additionally, or alternatively, the method can further include wirelessly transmitting one or more control commands to a processor remote from the remote communication device.

According to yet another aspect, a system includes a catheter, a catheter interface unit, and a remote communication device. The catheter includes a handle, a tip portion, a shaft having a proximal end region and a distal end region, the proximal end region coupled to the handle, and the distal end region coupled to the tip portion. The catheter interface unit includes a processing unit and a graphical user interface. The remote communication device is coupled to the proximal end region of the shaft of the catheter, the remote communication device including a user interface and a wireless transmitter in communication with the user interface to send one or more control commands to the processing unit of the catheter interface unit, the one or more control commands corresponding to a set of input options displayed on the graphical user interface.

In certain implementations, the distal end region of the shaft can be directly coupled to the tip portion.

In some implementations, movement of the user interface can be constrained in at least one direction with respect to the shaft of the catheter and the one or more inputs of the user interface are depressible in a direction parallel to the at least one constrained direction of the user interface.

In certain implementations, the remote communication device can be at least partially constrained in a radial direction relative to the shaft. For example, the user interface can be movable less than about 1 cm in the radial direction relative to the shaft. For example, the user interface can be entirely constrained in the radial direction relative to the shaft.

In some implementations, the user interface can be movable along an axis defined by the shaft of the catheter.

In certain implementations, the user interface can be rotatable about an axis defined by the shaft of the catheter. For example, the user interface can be rotatable relative to the handle.

In some implementations, the remote communication device can be coupled to the proximal end region of the shaft of the catheter at a fixed axial position of the shaft.

In certain implementations, the remote communication device can further include a housing, a portion of the housing defining a recess extending circumferentially about an outer surface of the shaft of the catheter. For example, the remote communication device can be coupled to the proximal end region of the shaft through an interference fit between the portion of the housing defining the recess and the proximal end region of the shaft of the catheter.

In some implementations, the remote communication device can be releasably coupled to the proximal end region of the shaft of the catheter.

In certain implementations, the catheter can further include an articulation controller supported on the handle, the articulation controller in mechanical communication with the shaft of the catheter to modify a position of the distal end region of the shaft. For example, the remote communication device can be distal to the articulation controller.

In some implementations, the remote communication device can be electrically and fluidically isolated from the handle and from the shaft of the catheter.

In certain implementations, the one or more inputs of the user interface can be positioned relative to the shaft of the catheter such that the one or more inputs are manipulatable by a hand of the user while the same hand of the user applies an axial force to the shaft.

In some implementations, the one or more inputs of the user interface can be positioned relative to the shaft of the catheter such that the one or more inputs are manipulatable by a hand of the user while the same hand of the user applies torque to the handle of the catheter.

Embodiments can include one or more of the following advantages.

In certain implementations, the graphical representation of the cavity of the patient's heart can be modified based on input commands received from the first input device and from the second input device. Thus, control of the graphical representation of the cavity can be advantageously split between two users. As compared to systems controllable by only a single user, the divided control provided by the first input device and the second input device can facilitate receiving direct input from the physician, which can result in more efficient modification of the graphical representation. Additionally, or alternatively, because the graphical representation can also be controlled by a technician operating the first input device, functionality associated with complex manipulation and/or modification of the graphical representation can be retained.

In some implementations, the second set of input options, represented on the second portion of the graphical user interface and interacted with by the second input device, can correspond to a current state of a state machine having a plurality of states. Because the state of the state machine changes dynamically according to a given set of events associated with the medical procedure and/or inputs from the second input device, robust functionality can be provided to the physician through relatively few inputs on the second input device. Such relatively few inputs on the second input device can be useful, for example, for facilitating one-handed operation of the second input device. Additionally, or alternatively, the relatively few inputs on the second input device can facilitate integrating the control functionality of the second input device into the handle of the catheter. Further in addition, or further in the alternative, the simple interface of the second input device can advantageously reduce the physician's need to look at the second input device, which can be useful for maintaining the physician's focus on the graphical user interface during a medical procedure.

Other aspects, features, and advantages will be apparent from the description and drawings, and from the claims.

BRIEF DESCRIPTION OF THE DRAWINGS

Like reference symbols in the various drawings indicate like elements.

DETAILED DESCRIPTION

The present disclosure is generally directed to devices, systems, and methods of facilitating a physician's interactions with a graphical user interface associated with a medical procedure being performed by the physician. For example, the devices, systems, and methods of the present disclosure can facilitate the physician's ability to modify a representation of a three-dimensional model on the graphical user interface autonomously (e.g., without assistance from a second person), without interfering with the physician's ability to control the catheter during the medical procedure. By way of non-limiting example and for the sake of clarity of explanation, the devices, systems, and methods of the present disclosure are described with respect to the use of a catheter in a heart cavity of a patient during a medical procedure (e.g., cardiac ablation). However, it should be appreciated that, unless otherwise specified or made clear from the context, the systems and methods of the present disclosure can be used for any of various different medical procedures in which it is desirable for a physician to interact with a graphical user interface autonomously while simultaneously maintaining control over the medical device used as part of the medical procedure.

As used herein, the term "physician" should be considered to include any type of medical personnel who may be directly interacting with a catheter as part of a medical procedure and is used interchangeably herein with the term "user." The term "treatment" should be considered to include any manner and type of medical procedure involving the use of a catheter and, therefore, should be considered to include diagnosis, treatment, and combinations thereof, unless otherwise specified or made clear from the context.

In the following description, it is understood that terms such as "first," "second," "top," "bottom," "up," "down," "right," "left," and the like, are words of convenience and are not to be construed as limiting terms.

Figure 1:
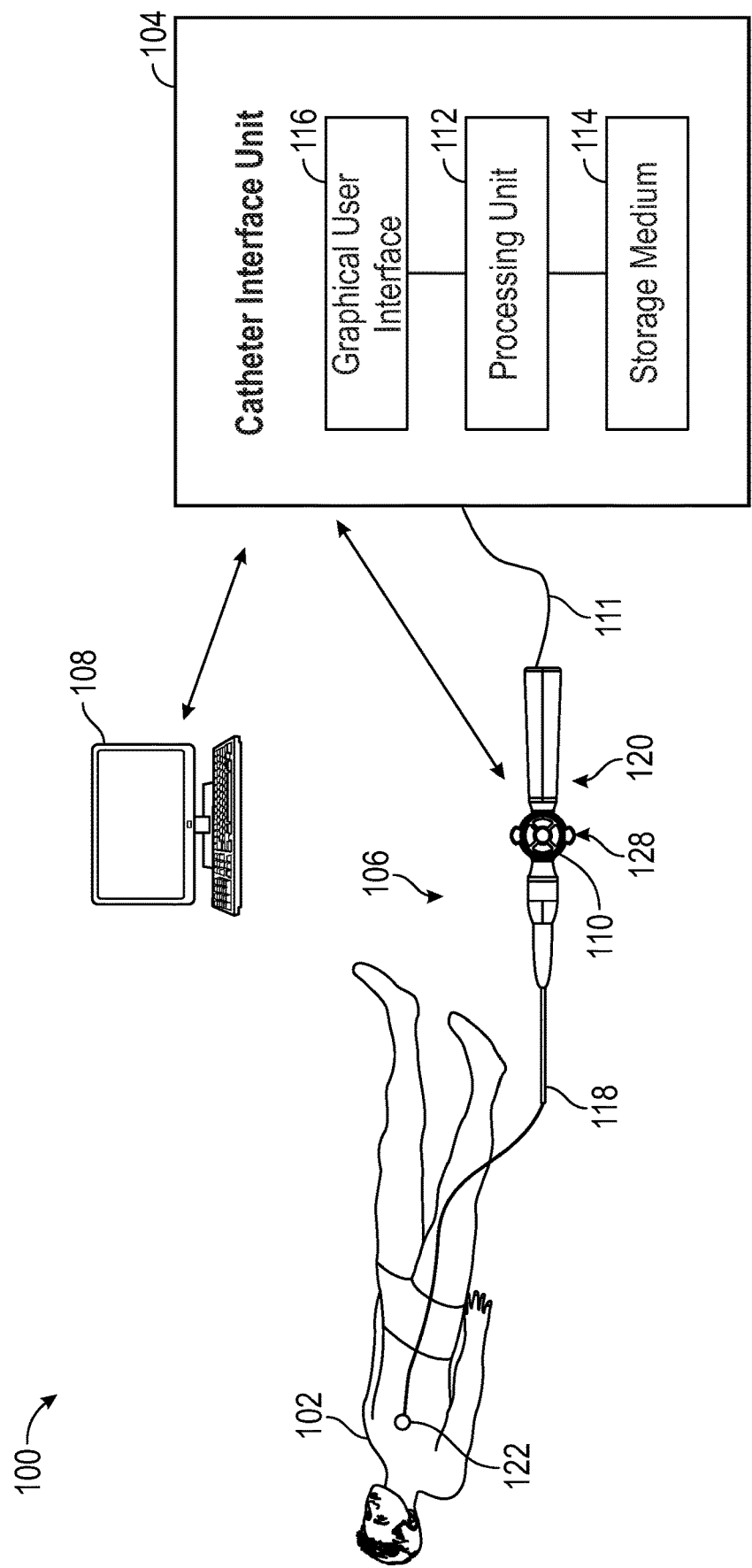
FIG. 1 is a schematic representation of a system during a medical treatment, the system including a catheter, a catheter interface unit, a first input device, and a second input device.

FIG. 1 is a schematic representation of a system 100 during a cardiac treatment (e.g., an ablation treatment) performed on a patient 102. The system 100 can include a catheter interface unit 104 in communication (e.g., wired or wireless communication) with a catheter 106, a first input device 108, and a second input device 110. For example, the catheter interface unit 104 can be in communication with the catheter 106 via an extension cable 111 and, additionally or alternatively, in wireless communication with one or more of the first input device 108 and the second input device 110. The catheter interface unit 104 can include a processing unit 112, a non-transitory, computer readable storage medium 114, and a graphical user interface 116. The processing unit 112 can be a controller including one or more processors, and the storage medium 114 can have stored thereon computer executable instructions for causing the one or more processors of the processing unit 112 to carry out one or more of the various methods described herein. In certain implementations, the catheter interface unit 104 can include additional features, including, without limitation, one or more of the following: current generation; magnetic field generation; magnetic field sensing, and the like.

The first input device 108 can be a computer (e.g., a desktop computer, a laptop computer, or both), or other, similar input device. The first input device 108 can be operated, for example, by a technician outside of a sterile field, while the second input device 110 can include a simple interface suitable for operation by the physician within the sterile field. As described in greater detail below, the catheter interface unit 104 can receive one or more input commands from the first input device 108 and from the second input device 110, in response to respective input options on the graphical user interface 116. Based on the received one or more input commands, the catheter interface unit 104 can modify a three-dimensional model of a heart cavity of the patient 102 displayed on the graphical user interface 116.

The input options available to be controlled by the second input device 110 on the graphical user interface 116 can be state-dependent, as also described in greater detail below, such that the second input device 110 can be used to interact extensively with the graphical user interface 116 through the use of only a few input sources (e.g., buttons) on the second input device 110. That is, the input options corresponding to the input sources on the second input device 110 at any given time during a medical procedure can be displayed on the graphical user interface 116. Advantageously, as also described in greater detail below, these input options can change according to a state of a state machine, which itself can change according to context (e.g., based on one or more previous actions, a current state, or a combination of both) and/or inputs. Thus, for example, the meaning of pressing a particular input source (e.g., pressing an "up" button) can change based on the state of the state machine, and the meaning of the particular input source at any given time can be displayed to the physician via the graphical user interface 116. Accordingly, as compared to systems in which controller actions are displayed on a handle of a device or on the controller itself and/or are otherwise fixed, the dynamic interaction between the second input device 110 and the graphical user interface 116 can facilitate the use of the state machine which, in turn, can facilitate achieving a given level of control over the graphical user interface 116 using fewer input sources on the second input device 110. With fewer input sources, the second input device 110 can be made into a form factor suitable for integration into a medical device such as the catheter 106, as described in further detail below.

It should be appreciated that, in implementations in which the second input device 110 includes only a few input sources, a physician can use the second input device 110 to interact with the graphical user interface 116 while maintaining control over the catheter 106 during the medical procedure and, thus, while remaining in a sterile field. In such implementations, it should be further appreciated that the limited number of input sources on the second input device 110 can make it easier for the physician to use the second input device 110 to interact with the graphical user interface 116 with less of a need to switch focus between the graphical user interface 116 and the second input device 110. Thus, for example, because the second input device 110 includes only a few input sources, the physician has less of a need to look at the second input device 110 during operation of the second input device 110. For at least this reason, the simplified inputs of the second input device 110 can facilitate continuous manipulation of the catheter 106 by the physician, particularly in instances in which the physician must look at the graphical user interface 116 to manipulate the catheter 106 during a medical procedure.

Figure 2:
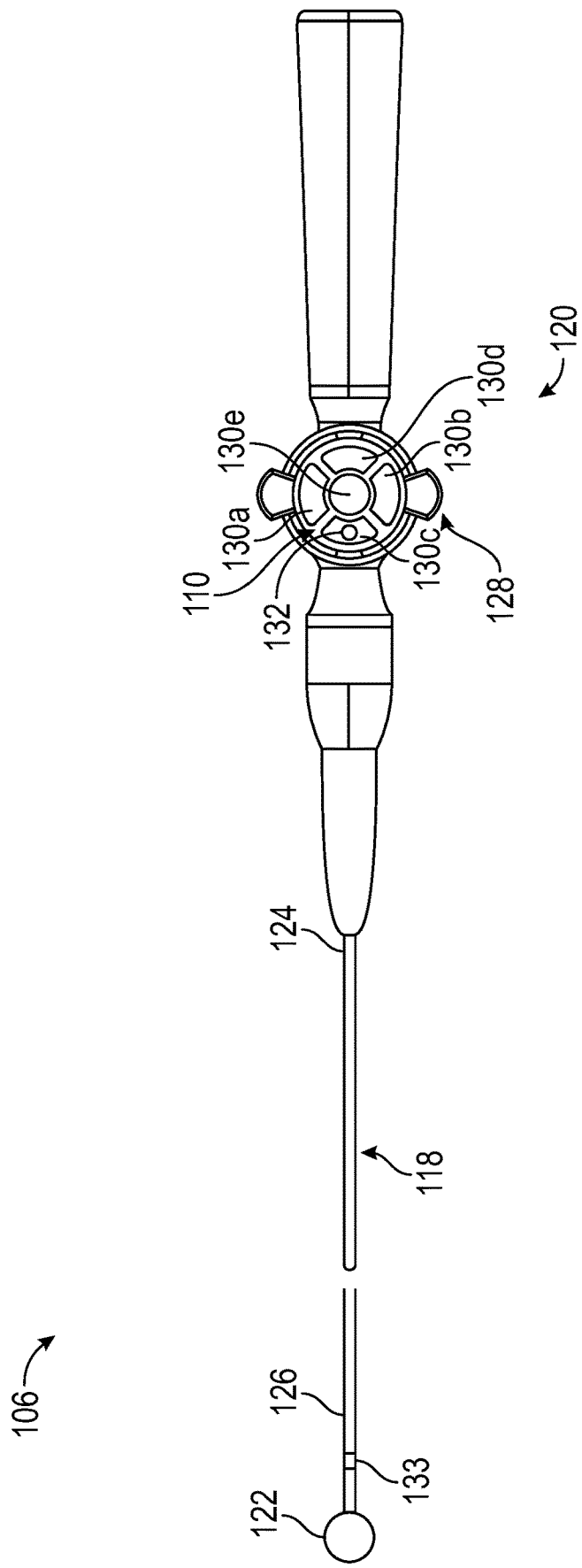
FIG. 2 is a top view of the catheter of the system of FIG. 1.

Referring now to FIGS. 1 and 2, the catheter 106 can include a catheter shaft 118, a handle portion 120, and a tip portion 122. The catheter shaft 118 includes a proximal end region 124 and a distal end region 126. The handle portion 120 is coupled to the proximal end region 124 and the tip portion 122 is coupled to the distal end region 126. The second input device 110 can be coupled to the handle portion 120 and can communicate with the graphical user interface 116 such that the second input device 110 should be understood to be a graphical user interface (GUI) controller according to all aspects of the present disclosure. An articulation controller 128 can also, or instead, be supported on the handle portion 120. Thus, as described in greater detail below, the second input device 110 can be operated to communicate with the catheter interface unit 104 (e.g., with the processing unit 112) such that commands received by the catheter interface unit 104 from the second input device 110 can form the basis of one or more changes to a three-dimensional model of a heart cavity of the patient 102 displayed on the graphical user interface 116 while the articulation controller 128 can be operated to move the tip portion 122 of the catheter 106 in the heart cavity.

The second input device 110 can be in remote communication with the graphical user interface 116 and, for example, can include a transmitter (e.g., a wired transmitter, a wireless transmitter, or both) for such remote communication. In implementations in which the second input device 110 includes a wired transmitter, communication between the second input device 110 and the catheter interface unit 104 can be via wires 111 extending from the catheter 106 to the catheter interface unit 104. In addition, or in the alternative, in implementations in which the second input device 110 includes a wireless transmitter, communication between the second input device 110 and the catheter interface unit 104 can include communication via any of various different known wireless communication protocols. An example of such a wireless communication protocol is Bluetooth®, a wireless standard available from Bluetooth SIG, Inc. While a standardized communication protocol, such as Bluetooth®, may be useful for pairing off-the-shelf hardware components, it should be appreciated that a customized communication protocol can be useful for avoiding interference with the communication between the second input device 110 and the catheter interface unit 104.

The form factor of the second input device 110 can be based on one or more of the size of the handle portion 120 and the orientation of the second input device 110 relative to the articulation controller 128. Thus, a small form factor of the second input device 110 can be desirable for sizing the handle portion 120, for example, for ease of operation by the physician (e.g., one-handed operation). To achieve a small form factor, the second input device 110 can include a small number of input options (e.g., less than ten) arranged relative to one another in a space-efficient and, or instead, intuitive manner. Additionally, or alternatively, it can be desirable to include a small number of input options on the second input device 110 to provide a simple interface that can be operated by the physician with little to no need for the physician's attention to move back and forth from the graphical user interface 116 to the second input device 110. That is, the simple interface provided by the second input device 110 can, in certain instances, be used by the physician without requiring the physician to look at the second input device 110, making it easier for the physician's attention to remain on the graphical user interface 116 during a medical procedure. It should be appreciated, however, that providing a physician with access to a diverse set of actions on the graphical user interface 116 can additionally, or alternatively, be desirable. To manage these competing design considerations, as described in greater detail below, the simple interface of the second input device 110 can cooperate with the graphical user interface 116 to provide the physician with state-dependent functionality, on the graphical user interface 116, which can be both useful for a given state of the medical procedure and easily navigated using the small number of inputs on the second input device 110.

The second input device 110 can include inputs 130a, 130b, 130c, 130d, 130e spatially arranged relative to one another to facilitate intuitive navigation, using the second input device 110, through one or more menus on the graphical user interface 116. The inputs 130a, 130b, 130c, 130d, can be discrete navigation inputs separate from one another. Thus, by way of non-limiting example, the navigation inputs 130a, 130b, 130c, 130d can be arranged in a right (130a), left (130b), up (130c), and down (130d) configuration relative to one another such that pressing the right navigation input 130a corresponds to navigation to the right in a menu displayed on the graphical user interface 116, pressing the left navigation input 130b corresponds to navigation to the left in a menu displayed on the graphical user interface 116, etc. Additionally, or alternatively, the input 130e can be an "enter" input and can be arranged, for example, substantially in the middle of the navigation inputs 130a, 130b, 130c, 130d. Further in addition, or further in the alternative, the press time and/or number of presses (e.g., single click versus double click) associated with pressing one or more of the inputs 130a, 130b, 130c, 130d, and 130e can be used to achieve further functionality of the second input device 110 using a limited number of inputs. For example, a long press time of one or more of the inputs 130a, 130b, 130c, 130d, and 130e can change a high level state of the state machine controlled by the second input device 110 while a short press time of one or more of the inputs 130a, 130b, 130c, 130d, and 130e can scroll through a lower level state of the state machine controlled by the second input device 110.

The navigation inputs 130a, 130b, 130c, 130d can be, in certain instances, buttons that are pressed to provide input to the second input device 110. Additionally, or alternatively, the second input device 110 can include a capacitive touch portion such that, for example, a sliding motion (e.g., of a finger) across the capacitive touch portion can be a navigation input transmitted by the second input device 110 to the graphical user interface 116. The capacitive touch portion can be arranged, in certain instances, as a circle such that a sliding motion detected around the circle is interpreted as a navigation input corresponding to scrolling (e.g., through a menu on the graphical user interface 116). Additionally, or alternatively, the capacitive touch portion can include any one or more of the inputs 130a, 130b, 130c, 130d, 130e. More generally, the inputs 130a, 130b, 130c, 130d, 130e can be any of various different types, alone or in combination with one another and can, in addition or optionally, be of any number useful for navigating through one or more menus displayed on the graphical user interface 116.

In some implementations, a combination of the number, size, and shape of the inputs 130a, 130b, 130c, 130d, 130e is such that the user can distinguish the buttons by feel. For example, given that the inputs 130a, 130b, 130c, 130d, 130e are in a constant position relative to one another and in a relatively constant position with respect to an axis defined by the catheter 106 (e.g., with respect to an axis defined by the catheter shaft 118). Accordingly, the inputs 130c and 130d are typically to the physician's right and left as the physician grips the handle 120. The inputs 130a and 130b can be in similarly predictable positions with respect to the physician's hand, given that the inputs 130a and 130b are in a fixed position relative to the inputs 130c and 130d.

In certain implementations, the second input device 110 can include an orientation feature 132 extending from a surface of the second input device 110. For example, the orientation feature 132 can extend from a surface of the up navigation input 130c. The orientation feature 132 can provide tactile feedback to the physician regarding the position of the physician's hand with respect to the second input device 110. Thus, in use, the physician can use tactile feedback from the orientation feature 132 to discern, without needing to look at the second input device 110, the position of the physician's hand with respect to the inputs 130a, 130b, 130c, 130d, 130e. This can be useful, for example, for facilitating switching back and forth, by the physician, between the operation of the articulation controller 128 and the second input device 110.

In general, the second input device 110 can be disposed relative to the articulation controller 128 along the handle portion 120. More generally, according to any one or more of the various different arrangements of the second input device 110 relative to the articulation controller 128 described herein, the physician can operate the second input device 110 to modify the graphical user interface 116 to achieve a desired view of the tip portion 122 of the catheter 106 on the graphical user interface 116 and, based on this desired view on the graphical user interface 116, can operate the articulation controller 128 to move the tip portion 122 of the catheter 106 to a desired location (e.g., into contact with tissue). In certain instances, the physician can control (e.g., maintain in place) the distal end region 126 of the catheter shaft 118 while simultaneously manipulating the second input device 110 according to any one or more of the methods described herein. Accordingly, it should be understood that such relative positioning of the articulation controller 128 relative to the second input device 110 along the handle portion 120 can include any of various different configurations that advantageously facilitate coordinated operation of the articulation controller 128 and the second input device 110.

In certain implementations, the second input device 110 can be disposed relative to the articulation controller 128 along the handle portion 120 such that the physician can manipulate the second input device 110 and the articulation controller 128 through one-handed operation. As used herein, one-handed operation should be understood to include manipulating the second input device 110 substantially simultaneously with manipulation of the articulation controller 128 using any combination of fingers of a single hand of the physician while the single hand of the physician maintains the same grip of the handle portion 120), leaving the physician with a free hand during the medical procedure. Such one-handed operation of the second input device 110 and the articulation controller 128 can be useful, for example, for allowing the physician to grip the catheter shaft 118 with a free hand to maintain the distal end region 126 in place in the heart cavity of the patient 102.

As an example, the second input device 110 can be coupled to the handle portion 120 at a position distal to the articulation controller 128 to facilitate operation of the articulation controller 128 with a thumb and manipulation of the second input device 110 with an index finger of the same hand while that hand maintains a natural grip of the handle portion 120.

Additionally, or alternatively, the second input device 110 can be coupled to the handle portion 120 along an axial position at which the articulation controller 128 is positioned on the handle portion 120. The articulation controller 128 can be movable, in certain instances, along a plane substantially perpendicular to a direction of movement of one or more of the inputs 130a, 130b, 130c, 130d, 130e. Such an orientation of the articulation controller 128 relative to the inputs 130a, 130b, 130c, 130d, 130e can be useful directing forces associated with manipulation of the articulation controller 128 in a direction different from a direction of forces associated with the one or more inputs 130a, 130b, 130c, 130d, 130e, which can facilitate substantially simultaneous but substantially independent operation of the articulation controller 128 and the one or more inputs 130a, 130b, 130c, 130d, 130e.

Further or instead, one or more inputs 130*a*, 130*b*, 130*c*, 130*d*, 130*e* can be positioned to facilitate other types of one-handed operation. For example, the one or more inputs 130*a*, 130*b*, 130*c*, 130*d*, 130*e* can be positioned relative to the catheter shaft 118 such that the one or more inputs 130*a*, 130*b*, 130*c*, 130*d*, 130*e* are manipulatable by a hand of the user while the same hand of the user applies an axial force to the catheter shaft 118 (e.g., through gripping the catheter shaft 118 between a thumb and another finger of a single hand). As an additional or alternative example, the one or more inputs 130*a*, 130*b*, 130*c*, 130*d*, 130*e* can be positioned relative to the catheter shaft 118 such that one or more inputs 130*a*, 130*b*, 130*c*, 130*d*, 130*e* are manipulatable by a hand of the user while the same hand of the user applies torque to the handle portion 120.

In some implementations, the second input device 110 can be rotatably coupled to the handle portion 120 such that the second input device 110 is rotatable about a circumference of the catheter shaft 118. In such implementations, operation of the second input device 110 and the articulation controller 128 can include rotating the second input device 110 relative to the catheter shaft 118 and, thus, relative to the articulation controller 128 to bring the second input device 110 into proximity to the articulation controller 128 and/or to the physician's hand during a procedure. Accordingly, it should be appreciated that rotation of the second input device 110 relative to the catheter shaft 118 can, in certain instances, facilitate one-handed operation of the second input device 110 and the articulation controller 128.

The second input device 110 can be, for example, rotatable (e.g., between zero degrees and about 180 degrees) about the circumference of the catheter shaft 118. As a more specific example, the second input device 110 can rotate freely about the circumference of the catheter shaft 118 such that the second input device 110 can be moved unimpeded about the circumference of the catheter shaft 118 through multiple rotations in any given direction. Such free rotation of the second input device 110 can facilitate moving the second input device 110 quickly into a desired position. For example, the physician can spin the second input device 110 into a desired position. Additionally, or alternatively, with free rotation about the catheter shaft 118, the physician can move the second input device 110 into place using any finger that might not otherwise be engaged during a medical procedure.

In some implementations, the second input device 110 can be releasably coupled to the handle portion 120. For example, a releasable coupling between the second input device 110 and the handle portion 120 can include a pin-and-socket configuration in which electrical communication and mechanical coupling between the second input device 110 and the handle portion 120 are established at substantially the same time as pins extending from the second input device 110 are inserted into corresponding sockets defined by the handle portion 120.

The second input device 110 can be sterilizable. For example, the second input device 110 can be formed of components compatible with sterilization according to one or more of the following sterilization techniques: ethylene oxide sterilization, autoclave sterilization, gamma radiation, gas-plasma sterilization. In implementations in which the second input device 110 is releasably coupled to the handle portion 120, the second input device 110 can be sterilizable separately from the handle portion 120. Further, or instead, the second input device 110 can be reusable such that the second input device 110 can be sterilized between uses and secured to a new handle portion 120 for each use.

The articulation controller 128 can be in mechanical communication with the catheter shaft 118. In operation, the articulation controller 128 can modify the position of the distal end region 126 of the catheter shaft 118 and, thus, modify the position of the tip portion 122 of the catheter 106. As an example, one or more pull wires (not shown) can couple the articulation controller 128 to the catheter shaft 118 as is known in the art.

Operation of the articulation controller 128 can move one or more of the pull wires in a proximal direction to create a deflection force at the distal end region 126 of the catheter shaft 118. For example, the articulation controller 128 can include one or more levers rotatable about an axis substantially perpendicular to an axis defined by the handle portion 120, with the rotation of the articulation controller 128 moving one or more of the pull wires to deflect the distal end region 126 of the catheter shaft 118. Additionally, or alternatively, the articular controller 128 can include a plunger (e.g., proximal or distal to the handle portion 120) movable along an axis substantially parallel to an axis defined by the handle portion 120, with proximal and distal movement of the articulation controller 128 moving one or more pull wires to move the distal end region 126 of the catheter shaft between a deflected position and a straight position. Because the tip portion 122 is coupled to the distal end region 126 of the catheter shaft 118, the deflection force at the distal end region 126 of the catheter shaft 118 can deflect the tip portion 122. While the articulation controller 128 has been described as being in mechanical communication with the catheter shaft 118 via one or more pull wires, it should be appreciated the articulation controller 128 can additionally, or alternatively, be in mechanical communication with the catheter shaft 118 through any one or more methods known in the art (e.g., through torque transmitted via a rotating member).

The catheter 106 can further, or instead, include a magnetic position sensor 133 along the distal end region 126 of the catheter shaft 118. The magnetic position sensor 133 can be any of various magnetic position sensors well known in the art and can be positioned at any point along the distal end region 126. The magnetic position sensor 133 can, for example, include one or more coils that detect signals emanating from magnetic field generators. One or more coils for determining position with five or six degrees of freedom can be used.

The magnetic field detected by the magnetic position sensor 133 can be used to determine the position of the distal end region 126 of the catheter shaft 118 according to one or more methods commonly known in the art such as, for example, methods based on using a sensor, such as the magnetic position sensor 133, to sense magnetic fields and using a look-up table to determine location of the magnetic position sensor 133. Because the tip portion 122 is coupled to the distal end region 126 of the catheter shaft 118 in a known, fixed relationship to the magnetic position sensor 133, the magnetic position sensor 133 can provide the location of the tip portion 122. While the location of the tip portion 122 is described as being determined based on magnetic position sensing, other position sensing methods can additionally or alternatively be used. For example, the location of the tip portion 122 can be additionally, or alternatively, based on impedance, ultrasound, and/or imaging (e.g., real time Mill or fluoroscopy).

The tip portion 122 can be one or more of a diagnostic tip and a treatment tip for directing energy (e.g., RF energy, ultrasound energy, chemical energy) toward tissue of the heart cavity. For example, the tip portion 122 can include at least one electrode mechanically coupled (e.g., directly coupled or indirectly coupled) to the distal end region 126 of the catheter shaft 118. The at least one electrode can be, additionally or alternatively, disposed along an expandable element coupled to the distal end region 126 of the catheter shaft 118.

Figure 3:
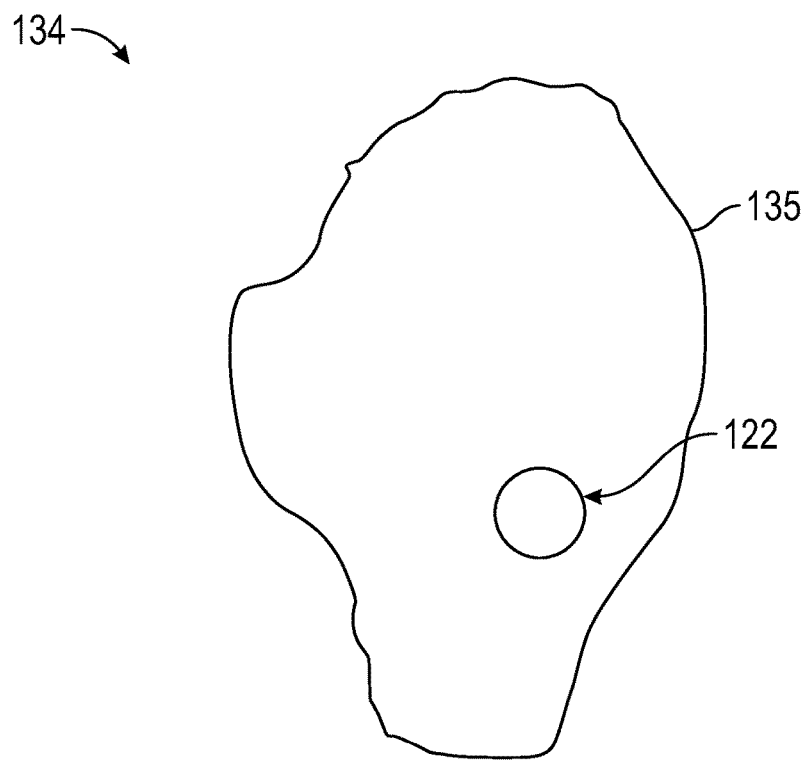
FIG. 3 is a schematic representation of a tip portion of the catheter of FIG. 2, with the tip portion depicted as inserted into a heart cavity of the patient of FIG. 1.

Referring now to FIG. 3, in use, the tip portion 122 can be inserted into a heart cavity 134 of the patient 102 (FIG. 2) as part of the medical procedure. In certain implementations, the tip portion 122 can interact with a surface 135 of the heart cavity 134 as part of a medical procedure. For example, the tip portion 122 can deliver energy to the surface 135 for the purpose of treatment, diagnosis, or both. The energy delivered through the tip portion 122 can include any manner and form of energy known in the art and, therefore, can include RF energy.

The location of the tip portion 122 relative to the surface 135 of the heart cavity 134 can be known (e.g., based on a signal received from the magnetic position sensor 133 of FIG. 2). Further, or in the alternative, the shape of the surface 135 of the heart cavity 134 can be known based on any of various different methods, including methods based on known locations visited by the tip portion 122 within the heart cavity 134. Accordingly, as described in greater detail below, the graphical user interface 116 can represent the location of the tip portion 122 relative to the surface 135 on the graphical user interface 116. Thus, in medical procedures in which direct visualization of the tip portion 122 in the heart cavity 134 is not possible, or is at least impractical, a physician can use the graphical user interface 116 as a tool for visualization of the tip portion 122 and/or the heart cavity 134 during a medical procedure.

Referring now to FIGS. 1-4, the graphical user interface 116 can include any of various different types of two-dimensional and/or three-dimensional displays known in the art. Thus, for example, the graphical user interface 116 can include a computer monitor or another similar type of two-dimensional display. Additionally, or alternatively, the graphical user interface 116 can include an augmented reality environment, a virtual reality environment, or combinations thereof.

The graphical user interface 116 can include a first portion 136 and a second portion 138 spatially delineated from the first portion 136. In general, the spatial delineation between the first portion 136 and the second portion 138 can facilitate accommodating two different use cases on the graphical user interface 116 at the same time. For example, the second portion 138 can work in cooperation with the limited inputs of the second input device 110 to provide the physician with a robust interface while the first portion 136 can cooperate with more expansive input options available through the first input device 108 (e.g., input options compatible with a full keyboard, a mouse, or combinations thereof). In general, these use cases are not interchangeable with one another as efficient input solutions. That is, it would be inefficient to use the second input device 110, with limited input options, to operate the first portion 136 of the graphical user interface 116, and the opposite case of operating the first input device 108, with multiple input options, to navigate through a state machine represented on the second portion 138 of the graphical user interface 116 is also an inefficient input solution. Accordingly, the spatial delineation between the first input portion 136 and the second input portion 138 can be useful for providing different users with user interface elements that are appropriate for a given use case associated with the respective user.

In certain implementations, spatial delineation of the first portion 136 from the second portion 138 can be useful for facilitating switching focus between the first portion 136 and the second portion 138 by a physician during a medical procedure. For example, because the second portion 138 is in a readily identifiable location (e.g., centered on the graphical user interface 116) relative to the first portion 136 on the graphical user interface 116, the physician can easily switch focus back and forth between the first portion 136 and the second portion 138 with little time and effort expended to locate or relocate the physician-specific interface on the second portion 138 of the graphical user interface 116. Further, or in the alternative, such spatial delineation of the first portion 136 from the second portion 138 can facilitate concurrent, or substantially concurrent, use of the graphical user interface 116 by two different users, as described in greater detail below.

The first portion 136 of the graphical user interface 116 can include a first set of input options 140 and, further or instead, a graphical representation 142 of the heart cavity 134. As used herein, the graphical representation 142 of the heart cavity 134 can include partial depictions of the heart cavity 134, such as those that may be generated in implementations in which the graphical representation 142 is built based on known locations of the catheter 106. The first set of input options 140 can correspond to permissible modifications and/or display settings of the graphical representation 142. Such modifications and/or display settings of the graphical representation 142 can correspond to one or more input commands based on the first set of input options 140 and received in preparation for and/or during a medical procedure.

Figure 4:
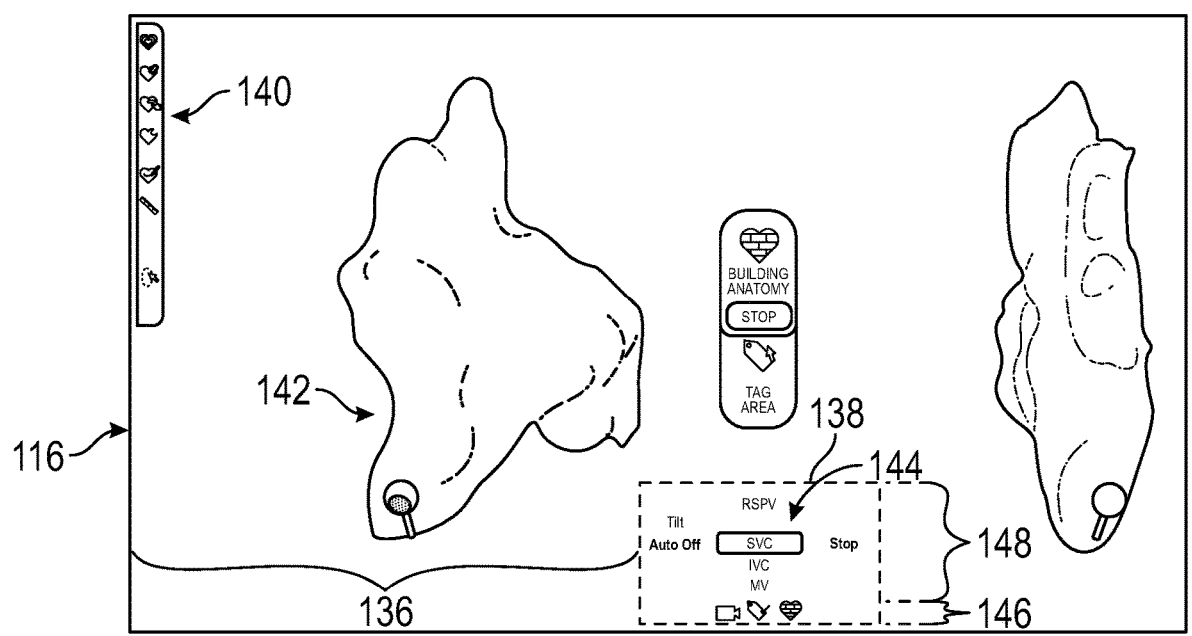
FIG. 4 is a schematic representation of a graphical user interface of the system of FIG. 1.

The graphical representation 142 can be based, for example, on the shape of the surface 135 of the heart cavity 134 such that the graphical representation 142 can include at least one two-dimensional projection of a three-dimensional model of the heart cavity 134. Additionally, or alternatively, the graphical representation 142 can include a depiction of a portion of the catheter 106 (e.g., the tip portion 122), which can be useful for locating the portion of the catheter 106 relative to the heart cavity 134. As shown in FIG. 4, the graphical representation 142 can include, for example, more than one two-dimensional projection of a three-dimensional model of the heart cavity 134, with each two-dimensional projection projected to a different image plane and, thus, corresponding to a different view of the three-dimensional model of the heart cavity 134.

The second portion 138 of the graphical user interface 116 can include a second set of input options 144. The second set of input options 144 can advantageously be different from the first set of input options 140, as described in greater detail below. In general, the second set of input options 144 can correspond to permissible modifications and/or display settings associated with the graphical representation 142 in the first portion 136 of the graphical user interface 116. Such modifications of the graphical representation 142 can correspond to one or more input commands based on the second set of input options 144 and received in preparation for and/or during a medical procedure.

The first input device 108 can be in communication with the first portion 136 of the graphical user interface 116 while the second input device 110 can be in communication with the second portion 138 of the graphical user interface 116. In general, a first user (e.g., a technician outside of a sterile field) can use the first input device 108 to interact with the first set of input options 140 on the graphical user interface 116, and a second user (e.g., a physician within a sterile field) can use the second input device 110 to interact with the second set of input options 144 on the graphical user interface 116 while concurrently, or substantially concurrently, manipulating the catheter 106. Because the second user can be constrained (e.g., by requirements for maintaining the sterile field and/or the need to manipulate the catheter 106), the second set of input options 144 can advantageously be state-dependent to facilitate navigation of the second set of input options 144 using only a limited number of inputs, such as the inputs 130a, 130b, 130c, 130d, 130e, of the second input device 110.

As used herein, the term "state-dependent" is inclusive of a state machine in which the second set of input options 144 can be in one of a set number of conditions, or states, based on one or more previous states and on previous inputs, with state transitions in such a state machine depending on the present state and the present inputs. Examples of a state-machine associated with the second set of input options 144 are described in greater detail below. In general, however, the second set of input options 144 can be state-dependent such that, although a given state of the second set of input options 144 may be a reduced set of options as compared to the first set of input options 140, the combination of the states of the second set of input options 144 can offer functionality equivalent or similar to the functionality available through all or a subset of the first set of input options 140.

The second portion 138 of the graphical user interface 116 can include, for example, a banner section 146 and a menu section 148. In combination, the banner section 146 and the menu section 148 can present the second set of input options 144 corresponding to the current state of a plurality of states of the state machine. Also, or instead, the combination of the banner section 146 and the menu section 148 can provide the physician with visual context for navigating to other states of the state machine. Such visual context can facilitate, for example, efficient navigation to the various states of the state machine (e.g., as necessitated during the medical procedure) using only a limited number of inputs, such as the inputs 130a, 130b, 130c, 130d, 130e of the second input device 110.

Figure 5:
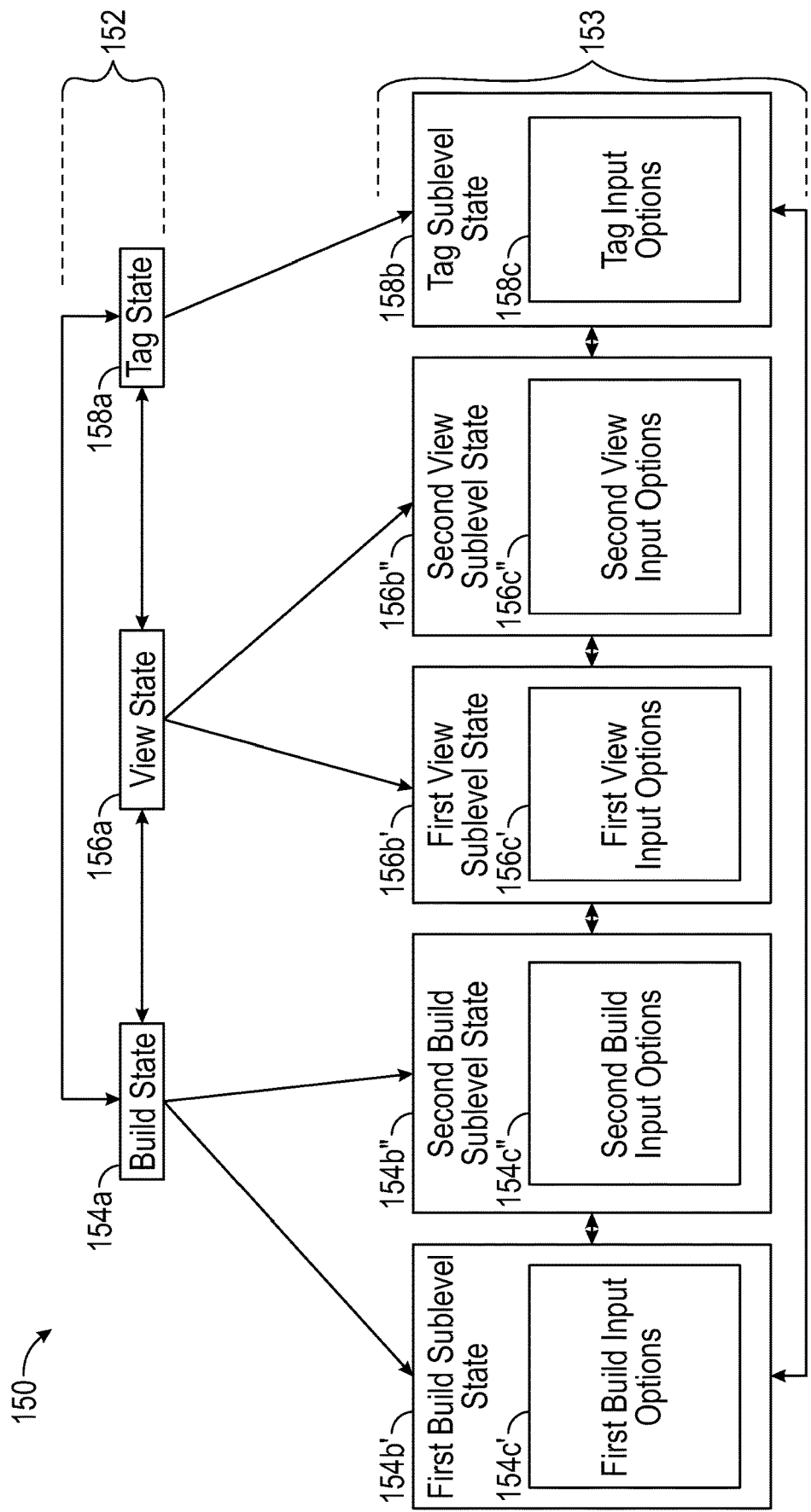
FIG. 5 is a schematic representation of a state machine corresponding to menu options on a second portion of the graphical user interface of FIG. 4.

FIG. 5 is a schematic representation of an example of a state machine 150 implemented on the catheter interface unit 104 (FIG. 1). For the sake of clarity of representation, the states of the state machine 150 are generally represented relative to one another in two-dimensions in FIG. 5. Each arrow between states of the state machine 150 represents a navigation input command that will move the state machine 150 from one state to another. Thus, in the example shown in FIG. 5, right/left navigation commands received from the second input device 110 (FIG. 2) move to the right or left, as the case may be, of a given state, and up/down navigation commands received from the second input device 110 (FIG. 2) move up or down, as the case may be, relative to a given state. It should be appreciated, however, that additional or alternative relationships between navigations inputs from the second input device 110 (FIG. 2) can be used to navigate through the states of the state machine 150. As an example, the press time (e.g., a long press time) associated with a navigation input command from the second input device 110 can be used to skip to a particular state in the state machine 150.

Referring now to FIGS. 1-5, as described in further detail below, the current state of the state machine 150 can be represented on the second portion 138 of the graphical user interface 116, and an adjacent state or states of the state machine 150 can be represented on the second portion 138 of the graphical user interface 116 (e.g., as a preview) to facilitate navigation from one state to another.

The state machine 150 can have any of various different configurations, which can depend on, among other things, the configuration of the second input device 110, the configuration of the second set of input options 144, the functionality to be provided to the physician, and/or the application to which the state machine is being applied. Accordingly, while specific implementations of the state machine 150 are described herein by way of example, further or alternative implementations of the state machine 150 are additionally or alternatively possible.

In general, the state machine 150 can include a top-level 152 and one or more sublevels 153. The functionality described herein with respect to the top-level 152 and the one or more sublevels 153 is by way of example and not limitation. Further, it should be appreciated that the state machine 150 can include a layer above the top-level 152 through which access to the state machine 150 is gained. For example, the state machine 150 can include one or more layers above the top-level 152 to allow the physician to choose between an ablation mode and a mode in which the physician can work with the state machine 150 to modify the graphical representation 142.

In the exemplary state machine 150, the top-level 152 includes a build state 154a, a view state 156a, and a tag state 158a (sometimes collectively referred to herein as "top-level states" and sometimes individually referred to herein as a "top-level state"). One or more sublevel state can be below each top-level state. For the sake of clarity, the hierarchy of states of the state machine 150 is represented in FIG. 5 such that each top-level state has an element number ending with "a," each sublevel state below the respective top-level state is represented with the same element number ending with "b" (in the case of a first sublevel state), and the input options corresponding to a given sublevel state are represented with the same element number ending with "c".

Navigation through the states of the state machine 150 can be represented in the second portion 138 of the graphical user interface 116 (e.g., as a change in the state highlighted in the second portion 138). In general, one or more of the inputs 130a, 130b, 130c, 130d, 130e of the second input device 110 can be used to send navigation commands to the catheter interface unit 104 to navigate through the states of the state machine 150 and one or more of the inputs 130a, 130b, 130c, 130d, 130e can be used to provide one or more input commands to the catheter interface unit 104 to select a particular state of the state machine 150. As navigation commands are sent to the catheter interface unit 104, the representation of the states of the state machine 150 on the second portion 138 of the graphical user interface 116 can change accordingly. For example, the second portion 138 of the graphical user interface 116 can highlight or otherwise accentuate the current navigation position of the state machine 150. In certain implementations, a received input command can select the current navigation position as the state of the state machine 150. Thus, as used herein, a "navigation command" should be understood to include an input sent from one or more of the inputs 130a, 130b, 130c, 130d, 130e to the catheter interface unit 104 to change a display of one or more states on the second portion 138 of the graphical user interface 116, with the change of the display of the one or more states corresponding to navigation through the states of the state machine 150. Additionally, or alternatively, an "input command" should be understood to include an input sent from one or more of the inputs 130a, 130b, 130c, 130d, 130e to the catheter interface unit to make a selection in the one or more displayed states on the second portion 138 of the graphical user interface 116.

Respective icons for the build state 154a, the view state 156a, and the tag state 158a can be displayed in the banner section 146 of the second portion 138 of the graphical user interface 116. These respective icons can advantageously provide a visual indication of the contents of the corresponding sublevel state displayed in the menu section 148 below the corresponding top-level state. For example, if an icon associated with the build state 154a is highlighted in the banner section 146, the physician can readily assess that the sublevel state shown in the menu section 148 corresponds to the build state 154a.

In use, the inputs 130a and 130b (right/left) can be used to provide navigation commands to scroll across the sublevel states in the state machine 150. It should be appreciated that scrolling across the sublevel states in the state machine 150 can be advantageous for efficient navigation at least because such scrolling reduces the need to use also the inputs 130c and 130d (up/down) to navigate to other sublevel states of the state machine 150. For example, the physician can use single button operation (e.g., using only the input 130a (right) or only the input 130b (left)) to scroll across the sublevel states. Scrolling across the sublevel states can be represented as a change in the sublevel state shown or highlighted in the menu section 148. Optionally, a corresponding change in the display of the icons of the top-level state can be shown in the banner section 146.

The inputs 130c and 130d (up/down) can be used to scroll through input options within a given sublevel state of the state machine 150, with the scrolling within the sublevel state represented as a change in the sublevel state option shown or highlighted in the menu section 148. For example, the inputs 130c and 130d (up/down) can be used to scroll through first build input options 154c' in the first build sublevel state 154b', second build input options 154c" in the second build sublevel, first view input options 156c' in the first view sublevel state, second view input options 156c" in the second view sublevel state 156b", and tag input options 158c in the tag sublevel state 158b.

As an example of navigation of the state machine 150, the physician can use the inputs 130a and 130b (right/left) to scroll from the tag sublevel state 158b to the view sublevel state 156b" to see options for adjusting the graphical representation 142 on the first portion 136 of the graphical user interface 116. This may be desirable, for example, for better visualization of the graphical representation 142 and, thus, for more accurate placement of tags on the graphical representation 142. As the physician scrolls from the tag sublevel state 158b to the view sublevel state 156b", the highlighted icon in the banner section 146 can change accordingly to provide the physician with a visual indication of the top-level state corresponding to the second set of input options 144. The physician can select the desired sublevel state, which is the view sub level state 156b" in this example, by providing an input command, such as an enter command via input 130e. With the desired sublevel state selected, the physician can use the inputs 130c and 130d (up/down) to scroll through input options associated with the selected sublevel state. It should be appreciated that other transitions between states of the state-machine 150 are additionally, or alternatively, possible and can similarly facilitate execution of the medical procedure by the physician.

The build state 154a can have a first build sublevel state 154b' and a second build sublevel state 154b". The state machine 150 can be in one or the other of the first build sublevel state 154b' and the second build sublevel state 154b", depending on whether a build procedure is in progress. As used herein, the build procedure can include formation of a three-dimensional model of the heart cavity 134 used to form the graphical representation 142 displayed on the graphical user interface 116. For example, the build procedure can be based on received locations of the tip portion 122 of the catheter 106 in the heart cavity 134.

The first build sublevel state 154b' can correspond to the build procedure being stopped. Accordingly, the first build sublevel state 154b' can include an input for starting the build procedure, which can be displayed in the menu section 148 of the second portion 138 of the graphical user interface 116. When the physician selects the input to start the build procedure, the current state of the state machine 150 can switch to the second build sublevel state 154b".

The second build sublevel state 154b" can correspond to the build procedure being in progress. Accordingly, the second build sublevel state 154b" can include an input for stopping the build procedure, which can be displayed in the menu section 148 of the second portion 138 of the graphical user interface 116. When the physician selects the input to stop the build procedure, the current state of the state machine 150 can switch to the first build level state 154b'. Thus, the state machine 150 moves between sublevel states (the first build sublevel state 154b' and the second build sublevel state 154b", in this example) to present the physician with input options that represent the next logical step or steps in the medical procedure, given the current state of the state machine 150.

The view state 156a can correspond to control of the graphical representation 142 on the first portion 136 of the graphical user interface 116. For the sake of clarity of explanation, the state machine 150 is described with respect to the view state 156a controlling a single view of the graphical representation 142. It should be appreciated, however, that the view state 156a can include multiple states, each corresponding to control of a different view of the graphical representation 142 on the first portion 136 of the graphical user interface 116. For example, in instances in which a first view of the graphical representation 142 is displayed on the left side of the graphical user interface 116 and a second view of the graphical representation 142 is displayed on the right side of the graphical user interface 116, the view state 156a can include states corresponding to the respective views on the left side and right side of the graphical user interface 116.

The view state 156a can include a first view sublevel state 156b' and a second view sublevel state 156b". While the view state 156a is described as having two sublevels, it should be appreciated that the view state 156a can have any of various different sublevels. In general, the sublevels associated with the view state 156a can depend on the amount of control to be provided to the physician with respect to the graphical representation 142 on the first portion 136 of the graphical user interface 116. Accordingly, the number of sublevels associated with the view state 156a can depend on the particular implementation. For example, in the case of implementations related to visualization of a medical procedure performed on the heart cavity 134 of the patient 102, the view state 156a can include a sublevel associated with rotation of the graphical representation 142 and a sublevel associated with one or more fixed views of the graphical representation 142.

The state machine 150 can be in one or the other of the first view sublevel state 156b' and the second view sublevel state 156b", depending on which of various, different view control features is selected. An example of a view control feature can be a fixed view mode in which a plurality of fixed views (e.g., left-anterior oblique (LAO), right-anterior oblique (RAO), etc.) are displayed in the menu section 148 such that the physician can scroll through the fixed views and select a desired view. Additionally, or alternatively, a view control feature can be an adjustable view mode (e.g., in which the physician can adjust a view parameter such as tilt). Accordingly, in implementations in which the first view sublevel state 156b' corresponds to a fixed view mode and the second view sublevel state 156b" corresponds to an adjustable view mode, the physician can switch between the fixed view mode and the adjustable view mode as desired (e.g., by scrolling across the sublevel states).

The tag state 158a can have, for example, a single tag sublevel state 158b including a selection of identifiers corresponding to anatomic features of the heart cavity. Thus, for example, when the top-level state of the state machine corresponds to the tag state 158a, the identifiers of the tag sublevel state 158b can be displayed in the menu section 148 of the second portion 138 of the graphical user interface 116. In use, the physician can navigate through the identifiers displayed in the menu section 148 using, for example, the inputs 130a, 130b, 130c, 130d and can select an identifier using the input 130e. As a result of this selection, an appropriate tag can appear on the graphical representation 142 shown on the first portion 136 of the graphical user interface 116. As an example, the appropriate tag can appear on the graphical representation 142 at a location based on the location of the catheter tip 122.

The tags available in the tag sublevel state 158b can be a function of the global state of the state machine 150 and, thus, can themselves be state dependent. For example, if the state machine 150 is in an "ablation" mode, the tags available in the tag sublevel state 158b can include tags related to marking the location of one or more ablations on the graphical representation 142. As an additional or alternative example, if the state machine 150 is in an "anatomy" mode, the tags available in the tag sublevel state 158b can correspond to marking anatomic features on the graphical representation 142. In cardiac implementations, the tags available in the tag sublevel state 158b can be dependent on the chamber of the heart in which the catheter 106 is inserted. For example, information regarding the chamber can be received from the first input device 108 and/or the second input device 110, and the tags in the tag sublevel state 158b can be updated accordingly.

The computer executable instructions stored on the computer readable storage medium 114 can cause the processing unit 112 to receive inputs from the first input device 108 and the second input device 110 to modify the graphical representation 142 according to one or more of the following exemplary methods. For example, the computer executable instructions stored on the storage medium 114 and executable by the processing unit 112 can be an application built using Visualization Toolkit, an open-source 3D computer graphics toolkit, available at www.vtk.org. Unless otherwise indicated or made clear from context, each of the following exemplary methods can be implemented using the system 100 and/or one or more components thereof.

Figure 6:
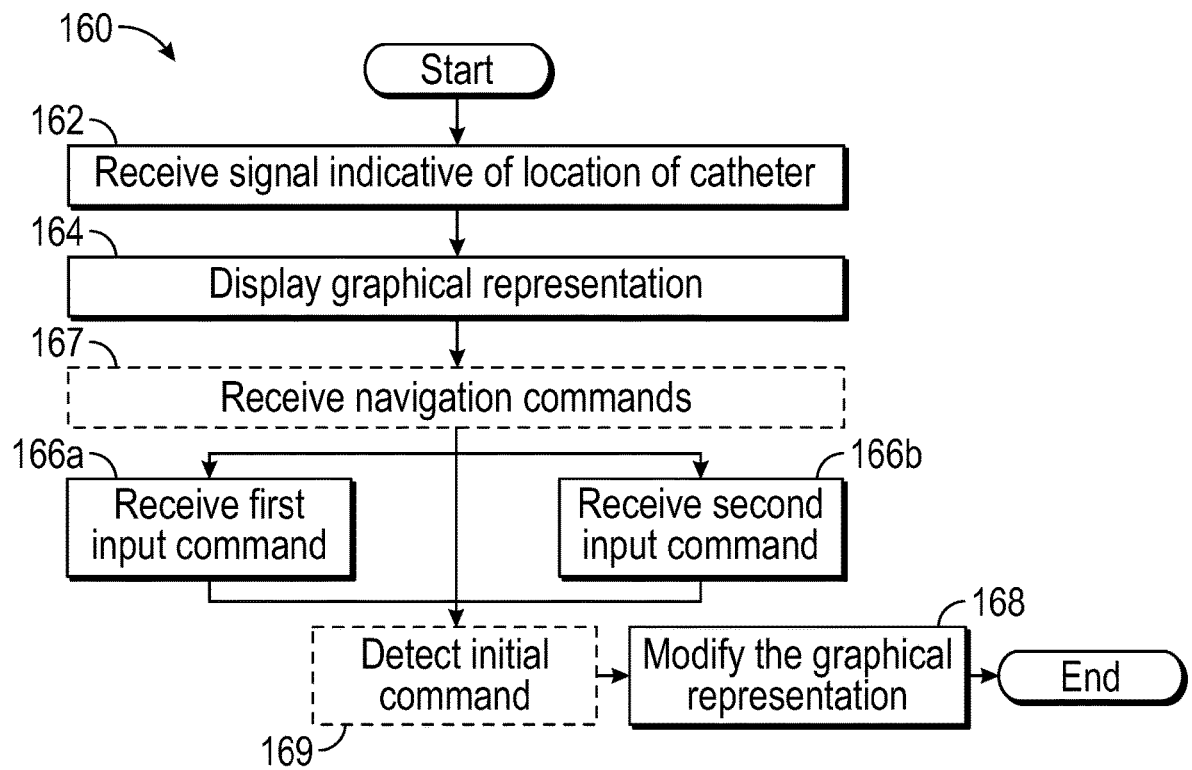
FIG. 6 is a flowchart of an exemplary method of controlling a graphical representation on the graphical user interface of the system of FIG. 1.

FIG. 6 is a flowchart of an exemplary method 160 of controlling a graphical representation on a graphical user interface. The graphical representation and the graphical user interface can be, for example, any of the various different graphical representations and graphical user interfaces described herein. Accordingly, the exemplary method 160 can control the display of the graphical representation 142 (FIG. 4) on the graphical user interface 116 (FIGS. 1 and 4).

The exemplary method 160 can include receiving 162 a signal indicative of location of a cardiac catheter in a cavity of a patient's heart, displaying 164 a graphical representation of the cavity of the patient's heart, receiving 166a a first input command based on a first set of input options, receiving 166b a second input command based on a second set of input options, and modifying 168 the graphical representation based on the first input command and on the second input command. The graphical representation can be based on the received 162 signal indicative of location of the cardiac catheter and can be displayed on a first portion of a graphical user interface, along with the first set of input options. The second set of input options can be displayed, for example, on a second portion of the graphical user interface.

Receiving 162 the signal indicative of location of the cardiac catheter in the cavity of the patient's heart can include any of the various different methods described herein for determining a location of a cardiac catheter in a heart cavity. For example, receiving 162 the signal indicative of location of the cardiac catheter in the cavity of the patient's heart can include receiving a signal from a sensor such as the magnetic position sensor 133 (FIG. 2). Further, it should be appreciated that the received 162 signal can be indicative of any predetermined location of the cardiac catheter in the heart cavity. Accordingly, the received 162 signal can be indicative of a tip portion (e.g., tip portion 122) of the cardiac catheter.

In certain implementations, displaying 164 the graphical representation of the cavity of the patient's heart can include projecting a model (e.g., a three-dimensional model) of either or both of the cardiac catheter and the cavity to an image plane corresponding to the graphical user interface. Further, or alternatively, displaying 164 the graphical representation can include displaying the cavity of the patient's heart in one or more views in the first portion of the graphical user interface. Such multiple views can be useful, for example, for visualizing movement of the cardiac catheter relative to one or more surfaces of the cavity.

In certain implementations, displaying 164 the graphical representation can include displaying only a graphical representation of the cardiac catheter initially, while a graphical representation of the heart cavity is being built. As the graphical representation of the heart cavity is built, displaying 164 the graphical representation can include updating the graphical representation to show the gradual generation of the graphical representation of the heart cavity.

Displaying 164 the graphical representation can be based on the received 166a first input command and the received 166b second input command. That is, in general, displaying 164 the graphical representation can be based on inputs received from two different sources. Such multiple inputs can be useful, for example, for facilitating receiving input directly from a physician while allowing a technician to provide additional or alternative inputs for controlling the graphical representation.

Receiving 166a the first input command from the first input device and receiving 166b the second input command from the second input device can occur concurrently. For example, receiving 166a the first input command can be along a first communication channel and receiving 166b the second input command can be along a second communication channel, different from the first communication channel. Each communication channel can be associated with a respective portion of the graphical user interface such that the first communication channel can be associated with the first portion of the graphical user interface, upon which the first set of input options is displayed and, similarly, the second communication channel can be associated with the second portion of the graphical user interface, upon which the second set of input options is displayed. It should be appreciated that during concurrent communication, one of the first communication channel or the second communication channel can have a predetermined priority over the other. For example, the second communication channel can be given priority over the first communication channel such that communication from the second input device associated with the physician is given priority over communication from the first input device.

One or both of receiving 166a the first input command from the first input device and receiving 166b the second input command from the second input device can include wireless or wired communication according to any of the various different communication systems and methods described herein. Further, one of the receiving 166a the first input command from the first input device and receiving 166b the second input command from the second input device can include wireless communication while the other includes wired communication.

Receiving 166a the first input command from the first input device can include receiving an input command from any of various different input devices known in the art, including, for example, one or more of a keyboard, a mouse, a touchscreen, etc. In general, the first input command can be received 156a from a technician, or other similar personnel, who is ordinarily not in the sterile field and, thus, ordinarily has full use of both hands to manipulate the first input device. Accordingly, the second set of input options can be a subset of the first set of input options such that the technician may have access to certain input options that are not available to the physician as the physician operates the second input device during the medical procedure. That is, the technician can have access to input options associated with functions that are more efficiently carried out by the technician than by the physician, who must also manipulate the catheter during the medical procedure.

The first set of input options from which the received 166a first input command is derived can be displayed along a portion of the graphical user interface that is ordinarily not an area of focus for the physician. For example, the first set of input options can be on the first portion of the graphical user interface and, optionally, set off to one side of the graphical representation of the heart cavity. It should be appreciated that such orientation of the first set of input options can be useful for efficient use of the space available on the graphical user interface. For example, because the first set of input options are not associated with the second input device operated by the physician, placing the first set of input options in a non-central location, or an otherwise deemphasized location, on the graphical user interface can facilitate presentation of the most relevant information to the physician during a medical procedure. That is, the second portion of the graphical user interface, upon which the second set of input options is displayed, can be substantially centrally positioned on the graphical user interface.

In general, receiving 166b the second input command can include receiving one or more commands from a remote device. As used herein, the term "remote device" includes an input device that is spatially separated from the first input device, from the graphical user interface, and/or from a processing unit of a catheter interface unit. In general, such spatial separation can be delineated by a sterile field such that the term "remote device" is inclusive of a device that transmits one or more input commands from within a sterile field to one or more portions of the system outside of the sterile field. Accordingly, it should be appreciated that remote communication using the remote device can offer certain advantages for communicating with a processing unit or other portions of a catheter interface unit while maintaining the sterile field.

Receiving 166b the second input command from the remote device can include receiving an input command from any of the various different remote devices described herein. Thus, for example, receiving 166b the second input command from the remote device can include receiving an input command from a second input device disposed on a handle portion of a catheter (e.g., the second input device 110 disposed on the handle portion 120 of the catheter 106 as described with respect to FIG. 2). Further, or in the alternative, receiving 166b the second input command from the remote device can include receiving an input command from a second input device that is separate from a catheter, as described in greater detail below.

Receiving 166b the second input command can include receiving a discrete selection command. The discrete selection command can include a click, or other similar discrete input appropriate for the second input device, corresponding to selection of one of the second set of input options. For example, the discrete selection command can include an input such as the input 130e arranged as an "enter" input as described with respect to FIG. 2. The instruction corresponding to the discrete selection command can vary depending on the state of a state machine represented in the second portion of the graphical user interface. More generally, the instruction corresponding to the discrete selection command can be based on the context of a particular portion of the medical procedure and, thus, can change over the course of the medical procedure.

In certain implementations, the exemplary method 160 can further include receiving 167 navigation commands for moving, within the second portion of the graphical user interface, between the options in the second set of options. As an example, the received 167 navigation commands can include discrete direction commands (e.g., left, right, up, and down corresponding to input from one or more of inputs 130a, 130b, 130c, 130d, and 130e) in the second portion of the graphical user interface. Because the physician may have to manipulate the catheter while providing the navigation commands, such discrete direction commands can facilitate navigating through the second portion of the graphical user interface through a simplified user interface manipulated, for example, through one-handed operation by the physician.

The navigation commands can be received before and/or concurrently with receiving 156b the second input command. For example, one or more of the received 167 navigation commands and the received 156b second input command can be used to navigate through the various different states of a state machine according to any one or more of the systems and methods described herein and, in particular, with respect to FIG. 5.

At least one of the received 167 navigation commands can scroll through the second set of input options displayed as an infinite wheel. That is, repeated receipt 167 of a particular navigation command (e.g., a "left" command) can cycle through the second set of input options continuously. Such continuous cycling in response to repeated receipt 167 of a particular navigation command can facilitate one-handed operation of the second input device to navigate the second set of input options. For example, if the physician inadvertently scrolls past a desired input option, the physician can continue to press the same navigation input (e.g., input 130a, 130b, 130c, 130d of FIG. 2) until the desired input appears again in the second portion of the graphical user interface.

In some implementations, the exemplary method 160 can further include detecting 169 receipt of an initial command. The initial command can be the received 166b second input command. By way of non-limiting example, the detected 169 receipt of the initial command can follow a period of inactivity and/or a predetermined change in the second portion of the graphical user interface. Additionally, or alternatively, the initial command can be one of the received 167 navigation commands.

In general, the first portion is viewable on the graphical user interface at the same time that the second portion is viewable on the graphical user interface, and it can be useful to delineate between the first portion and the second portion during the medical procedure. As an example of such a delineation between the first portion and the second portion, one or more display features of the second portion of the graphical user interface can be changed based on the detected 169 receipt of the initial command. Such a change in the second portion of the graphical user interface can advantageously provide the physician with feedback regarding proper operation of the second input device. That is, as the one or more display features of the second portion of the graphical user interface change, the change in the second portion of the graphical user interface can be perceived by the physician and, thus, serve as an indication that the commands from the second input device are being reflected in the second portion of the graphical user interface.

Changes to the one or more display features of the second portion of the graphical user interface can include displaying additional input options of the second set of input options (e.g., displaying additional input options related to a current state of the state machine such as the state machine 150 described with respect to FIG. 5). For example, detecting 169 receipt of the initial command can result in expansion of a menu to provide the physician with a visual representation of additional options. Additionally, or alternatively, detecting 169 receipt of the initial command can result in displaying one or more menus to provide the physician with a preview of menus that are adjacent to a current menu to facilitate navigation to an appropriate menu in the second portion of the graphical user interface.

In certain implementations, changing one or more display features of the second portion of the graphical user interface can include changing one or more display features of the second portion of the graphical user interface, relative to the first portion of the graphical user interface, between a baseline configuration and a modified configuration. As an example, such a change can include changing the size of the second portion of the graphical user interface relative to the size of the first portion of the graphical user interface. Thus, in such instances, detecting 169 receipt of the initial command can result in the second portion of the graphical user interface increasing in size relative to the first portion of the graphical user interface. This change in size can make the second portion of the graphical user interface easier to perceive by the physician and, thus, can facilitate navigation through one or more menus displayed on the second portion of the graphical user interface.

In addition to, or as an alternative to, changing the size of the second portion of the graphical user interface in response to detecting 169 receipt of the initial command, changing the one or more display features of the second portion of the graphical user interface can include changing opacity of the second portion of the graphical user interface relative to the opacity of the first portion of the graphical user interface. As an example, the baseline configuration of the second portion of the graphical user interface can be relatively opaque prior to detecting 169 receipt of the initial command and can become less opaque upon detecting 169 receipt of the initial command. Such a change in opacity of the second portion of the graphical user interface can make the second portion of the graphical user interface more easily perceivable by the physician.

Further in addition, or further in the alternative, changing one or more display features of the second portion of the graphical user interface relative to the first portion of the graphical user interface can include changing the position of the second portion of the graphical user interface relative to the position of the first portion of the graphical user interface. An example of such a change in position can include displaying the second portion of the graphical user interface as a pop-up window. For example, the pop-up window can appear in front of the first portion of the graphical user interface. More generally, a change in position of the second portion of the graphical user interface relative to the first portion of the graphical user interface can facilitate prominently displaying the second portion of the user interface for improved perceptibility by the physician during the medical procedure.

In some implementations, changing the one or more display features of the second portion of the graphical user interface relative to the first portion of the graphical user interface can include changing the second portion of the graphical user interface from the modified configuration to the baseline configuration if a time between receipt 169 of the initial command and receipt of a subsequent input command exceeds a predetermined inactivity threshold period. For example, the predetermined inactivity threshold period can be programmable (e.g., by the physician according to the physician's preference). Such a period of inactivity can coincide with the physician moving the catheter within the heart cavity. Accordingly, during this period, the second portion of the graphical user interface can be advantageously deemphasized in favor of a more prominent display of the first portion of the graphical user interface, which includes the graphical representation of the heart cavity.

In certain implementations, changing the one or more display features of the second portion of the graphical user interface relative to the first portion of the graphical user interface between the baseline configuration and the modified configuration can include changing the second portion of the graphical user interface from the modified configuration to the baseline configuration based on a received input command of the second set of input commands. Further, or in the alternative, a received input command of the second set of input commands can toggle between the modified configuration and the baseline configuration. Toggling between the modified configuration and the baseline configuration can, for example, provide the physician with control over the display of the second portion of the graphical user interface. Such control can be useful for deemphasizing the second portion of the graphical user interface on command to facilitate observation of the first portion of the graphical user interface by the physician (e.g., during a particular portion of the medical procedure).

In general, modifying 168 the displayed graphical representation in the first portion of the graphical user interface can include any one or more of various different changes to the displayed graphical representation that may improve visualization of the graphical representation by the physician. For example, modifying 168 the displayed graphical representation can include building a graphical representation of the heart cavity, altering a display view of the graphical representation, and/or tagging one or more anatomic features on the graphical representation. Because modifying 168 the displayed graphical representation can be based on the received 166a first input command from the first input device and the received 166b second input command from the second input device, it should be appreciated that relatively simple modifications 168 of the displayed graphical representation can be implemented through the second input device operated by the physician while more complex modifications 168 of the displayed graphical representation can be implemented through the first input device operated by the technician.

Modifying 168 the displayed graphical representation in the first portion of the graphical user interface can include, for example, modifying a pose of the graphical representation including one or more of a translation and an orientation. For example, the pose can include two rotation angles. The pose can correspond to one or more predetermined poses of the graphical representation. Further, or in the alternative, the pose can be customizable according to one or more inputs from one or both of the first input device and the second input device. In certain implementations, modifying 168 the displayed graphical representation can include adjusting an orientation of a displayed view of the graphical representation of the heart cavity such as, for example, by rotating the graphical representation of the heart cavity about an axis.

In certain implementations, modifying 168 the displayed graphical representation in the first portion of the graphical user interface can include adjusting the displayed graphical representation according to the order in which the first input command the second input command are received. Such modification 168 of the displayed graphical representation can allow the physician to undo or otherwise modify an input command provided by the technician through the first input device. More generally, the first input command and the second input command can operate in concert to modify 168 the displayed graphical representation.

Figure 7:
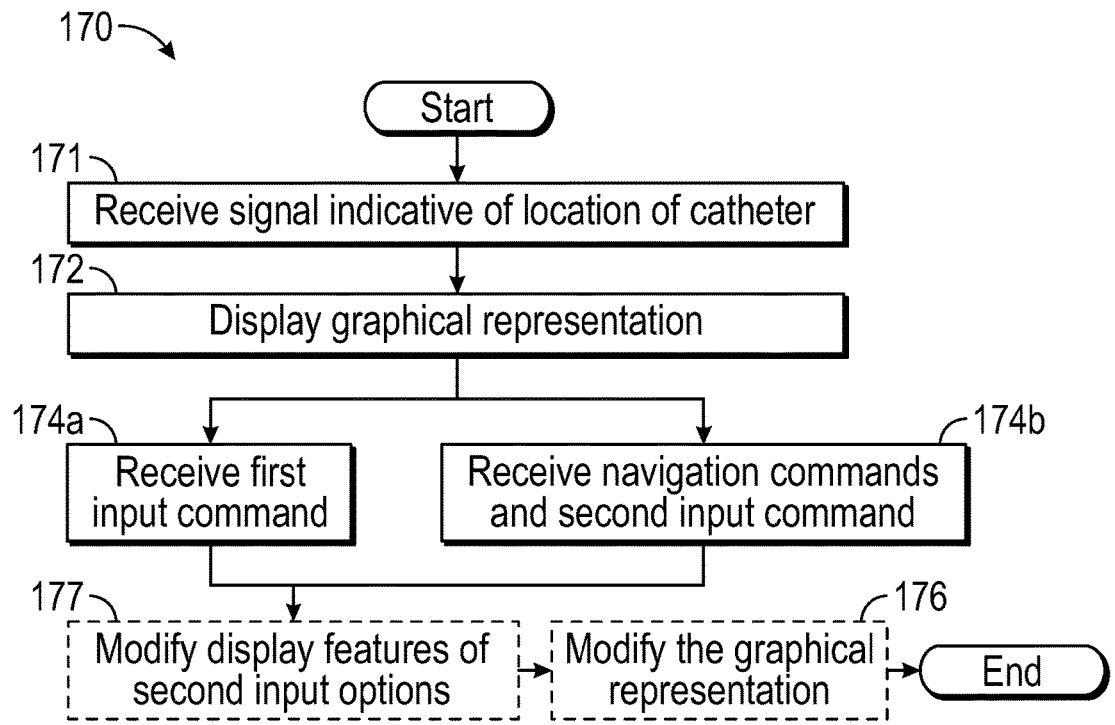
FIG. 7 is a flowchart of an exemplary method of controlling a graphical representation on the graphical user interface of the system of FIG. 1.

FIG. 7 is a flowchart of an exemplary method 170 of controlling a graphical representation on a graphical user interface. The graphical representation and the graphical user interface can be, for example, any of the various different graphical representations and graphical user interfaces described herein. Accordingly, the exemplary method 170 can control the display of the graphical representation 142 (FIG. 4) on the graphical user interface 116 (FIGS. 1 and 4).

The exemplary method 170 can include receiving 171 a signal indicative of a location of a catheter tip in a cavity of a patient's heart, displaying 172, on a graphical user interface, a graphical representation of the location of the catheter tip in the cavity of the patient's heart, receiving 174a a first input command from a first input device, receiving 174b navigation commands and a second input command from a second input device, and modifying 176 the displayed graphical representation based on the first input command and the second input command. The first input command can be responsive to a first set of input options displayed on the graphical user interface, and the second input command can be responsive to a second set of input options displayed on the graphical user interface.

Receiving 171 the signal indicative of the location of the catheter tip in the cavity of the patient's heart can include any one or more of the various different methods of receiving location information described herein. For example, receiving 171 the signal indicative of location of the cardiac catheter in the cavity of the patient's heart can include receiving a signal from a sensor such as the magnetic position sensor 133 (FIG. 2). Further, it should be appreciated that the received 171 signal can be indicative of any predetermined location of the cardiac catheter in the heart cavity. Accordingly, the received 171 signal can be indicative of a location of a tip portion (e.g., tip portion 122) of the cardiac catheter.

Displaying 172 the graphical representation of the cavity of the patient's heart on the graphical user interface can include any of the various different methods of displaying the graphical representation described herein. Accordingly, as an example, displaying 172 the graphical representation can include displaying a two-dimensional projection of a three-dimensional model of the cavity of the patient's heart. Additionally, or alternatively, displaying 172 the graphical representation of the cavity of the patient's heart on the graphical user interface can include displaying one or more views of the graphical representation.

The first input command can be received 174a from the various different devices and systems described herein with respect to the first input device and, additionally or alternatively, according to any one or more of the various different methods described herein with respect to sending and receiving a first input command from the first input device. Thus, for example, the first input command can be received 174a by a catheter interface unit via wired or wireless communication with a keyboard and/or mouse operated by a technician (e.g., outside of a sterile field). The first input command can be received 174a from among the first set of input options, which can be a full complement of possible input commands available for modifying the displayed 172 graphical representation of the cavity of the patient's heart. Additionally, or alternatively, the first set of input options can be displayed on a dedicated portion of a graphical user interface, away from the second set of input options, according to any of the various different methods described herein. Accordingly, the first set of input options can be displayed on the first portion of the graphical user interface, and the second set of input options on a second portion of the graphical user interface.

The navigation commands and/or the second input command can be received 174b from the various different devices and systems described herein with respect to the second input device and, additionally or alternatively, according to any one or more of the various different methods described herein with respect to sending and receiving navigation commands and/or a second input command from the second input device. For example, the navigation commands and the second input command can be received 174b by a catheter interface unit in wired or wireless communication with a second input device operated by a physician. The second input device can be any of the various different second input devices described herein.

In general, the second input device can include relatively few inputs as compared to the first input device, with the functionality of the second input device being a function of the representation of a state machine on the graphical user interface. For example, the second set of input options displayed on the graphical user interface can be based at least in part on the current state of the state machine and, additionally or alternatively, can include available transitions of a state machine. Continuing with this example, the navigation input commands received 174*b* from the second input device can be used to navigate through the transitions of the state machine and an input command received 174*b* from the second input device can be used to select a particular state of the state machine. Accordingly, it should be appreciated that the changing state of the state machine can impart additional functionality to the inputs of the second input device. That is, the result produced by a given received 174*b* input command can vary according to the state of the state machine at the time the input command is received 174*b*.

Receiving 174*b* the navigation commands and the second input command from the second input device can include receiving discrete commands. For example, the discrete commands can include commands for moving through the second set of input options. Examples of such discrete directional commands can include commands corresponding to right, left, up, and down navigation through the second set of input commands displayed in the second portion of the graphical user interface.

Also, or instead, receiving 174*b* the navigation commands and the second input command from the second input device can include receiving one or more analog commands. As an example, one or more inputs of the second input device can include a capacitive touch sensor that produces an analog input command. This analog command can be used, in certain instances, for navigating through the second set of input options. For example, in implementations in which the capacitive touch sensor is arranged as a scroll wheel, the scroll wheel can be used to scroll through the second set of input options.

The second set of input options can be arranged in an infinite wheel according to any of the arrangements described herein. In such implementations, receiving 174*b* the navigation commands can include receiving a scroll command (e.g., a discrete command, an analog command, or a combination thereof) for moving through the states of the infinite wheel. Thus, for example, a physician can press a single input on the second input device repeatedly, or by holding down the single input, to continually move through the infinite wheel until a desired input command is highlighted and can be selected.

Modifying 176 the displayed graphical representation can include any one or more of the various different modifications described herein. Accordingly, as an example, modifying 176 the displayed graphical representation can be based on the order in which the first input command and the second input command are received. Thus, in this example, the second input command can override a modification made based on the first input command and, in this way, can provide the physician with a mechanism for overriding a change made by the technician. Also, or instead, in instances in which the first input command and the second input command are received at the same time or substantially the same time, the second input command can override the first input command to reduce the likelihood that the second input command (associated with the physician) is inadvertently overwritten or otherwise undone by the first input command.

In some implementations, the exemplary method 170 can further include modifying 177 one or more display features of the second set of input options based on the received 174*b* navigation command and/or second input command. Modifying 177 the one or more display features of the second set of input options can be based, for example, on detecting an initial navigation or initial input command (e.g., after some predetermined period of inactivity). Additionally, or alternatively, modifying 177 the one or more display features of the second set of input options can include changing the second set of input options from the modified configuration to the baseline configuration if a time between receipt of a first input command and receipt of a second input command exceeds a predetermined inactivity threshold period.

In general, modifying 177 the one or more display features of the second set of input options can include changing between a baseline configuration and a modified configuration of the display features according to any of the various different methods described herein. Thus, for example, the relative size of the displayed second set of input options to the size of the displayed first set of input options can be greater in the modified configuration than in the baseline configuration to facilitate reading the second set of input options by the physician. In addition, or in the alternative, the opacity of the displayed second set of input options compared to the opacity of the first set of input options can be greater in the modified configuration than in the baseline configuration to facilitate drawing the physician's attention to the appropriate location on the graphical user interface. Additionally, or alternatively, the position of the second set of input options relative to the first set of input options on the graphical user interface can be different in the modified configuration than in the baseline configuration, with the change in position, for example, advantageously drawing the physician's attention toward the second set of input options.

While certain implementations have been described, other implementations are additionally or alternatively possible.

Figure 8:
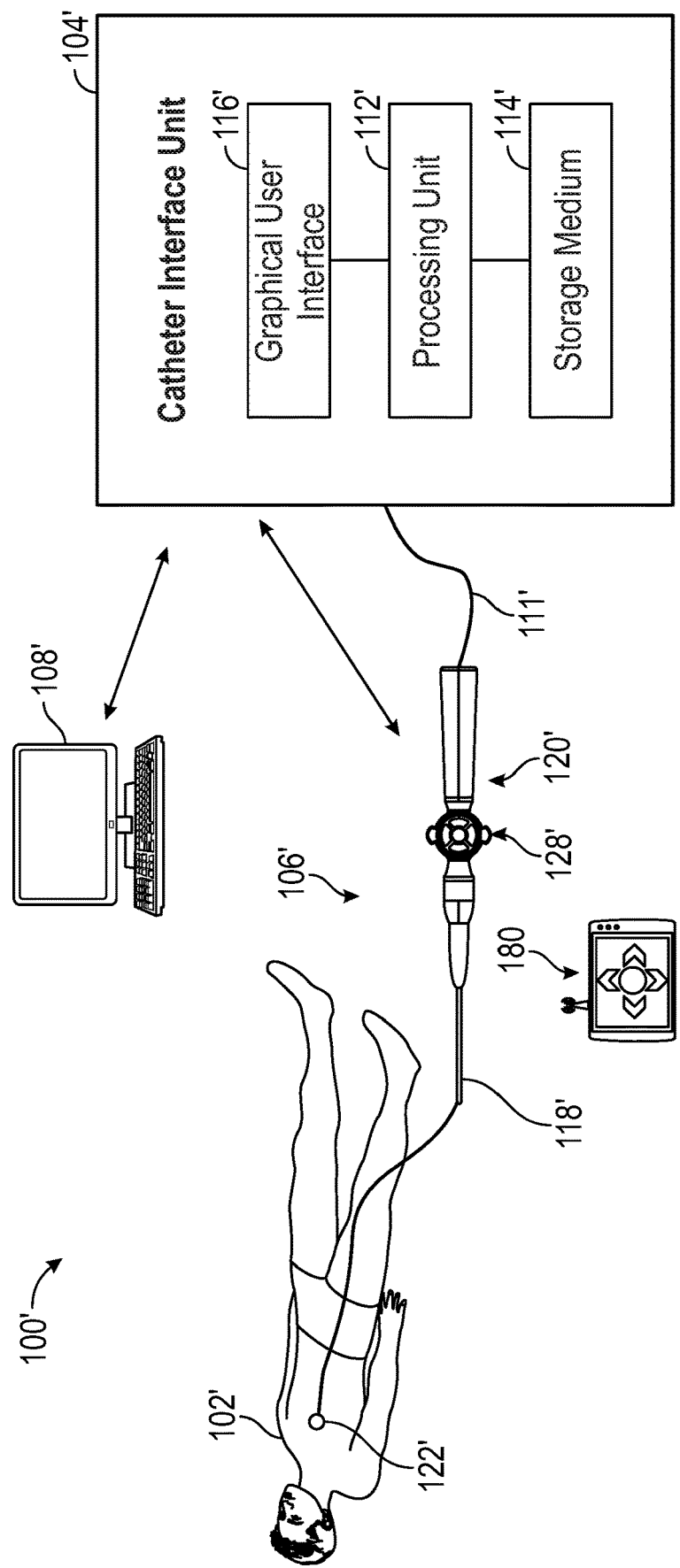
FIG. 8 is a schematic representation of a system during a medical treatment, the system including a catheter, a catheter interface unit, a first input device, and a second input device separate from the catheter.

For example, while a second input device has been described as being disposed along a handle of a catheter, other implementations are additionally or alternatively possible. As an example, referring now to FIG. 8, a system 100' can include a second input device 180 separate from a catheter 106'. For the sake of efficient and clear description, elements designated by prime (') element numbers in FIG. 8 should be understood to be analogous to elements with unprimed element numbers described herein, unless otherwise indicated or made clear from the context, and, thus, are not described separately from primed or unprimed counterparts, except to highlight certain aspects. Thus, for example, element number 116' in FIG. 8 should be understood to be a graphical user interface analogous to the graphical user interface 116 (FIGS. 1 and 4), unless otherwise indicated or made clear from the context.

The second input device 180 can be, for example, in communication with the catheter interface unit 104' to transmit navigation commands and/or input commands to a second portion of the graphical user interface 116' according to any of the various different methods described herein. Because the second input device 180 is not disposed along the catheter 106', the second input device 180 can be advantageously in wireless communication with the catheter interface unit 104' to reduce the number of wires in the vicinity of the physician during the medical procedure.

In general, the second input device 180 can be manually operable by the physician while the physician manipulates the catheter 106'. For example, the physician may pick up the second input device 180 as needed, and then put the second input device 180 down if both hands are needed for manipulation of the catheter 106'.

Figure 9:
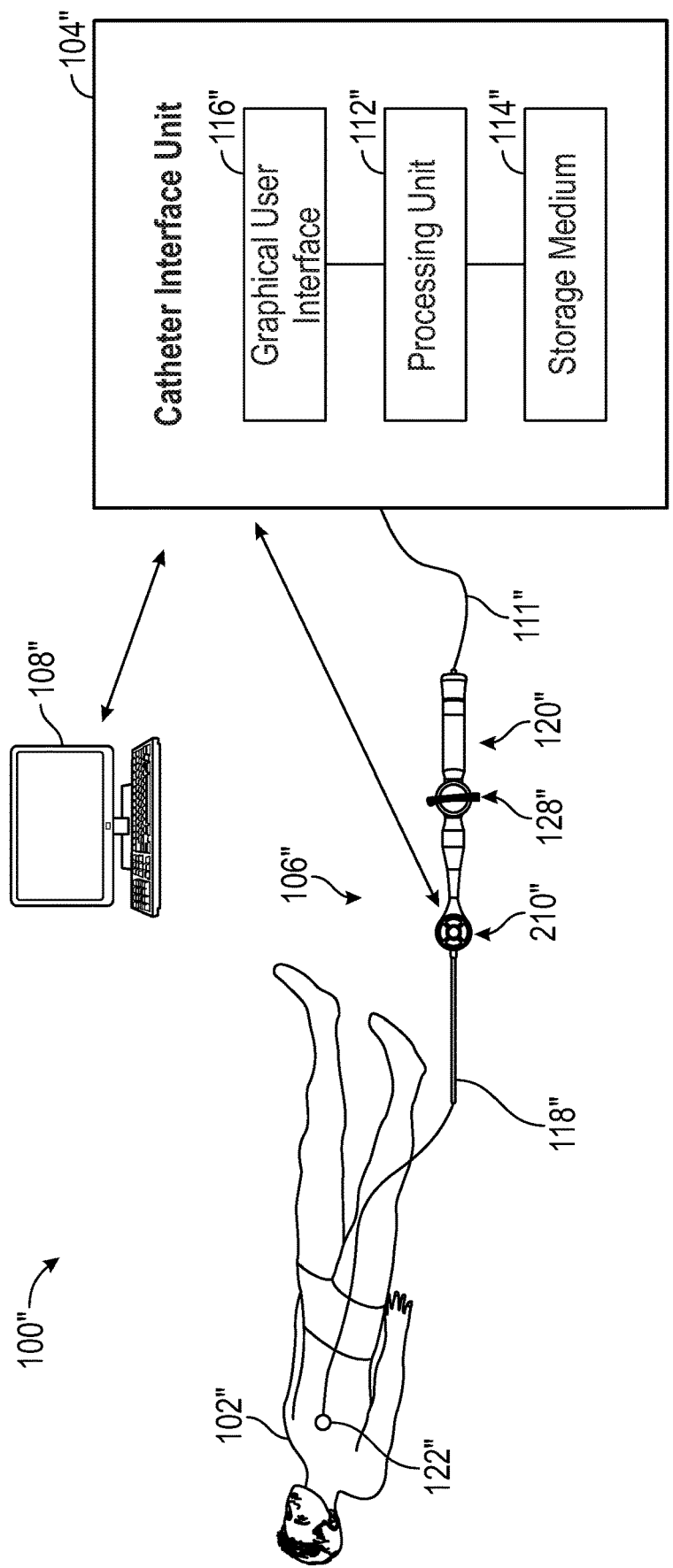
FIG. 9 is a schematic representation of a system during a medical treatment, the system including a catheter, a catheter interface unit, a first input device, and a second input device.
Figure 10:
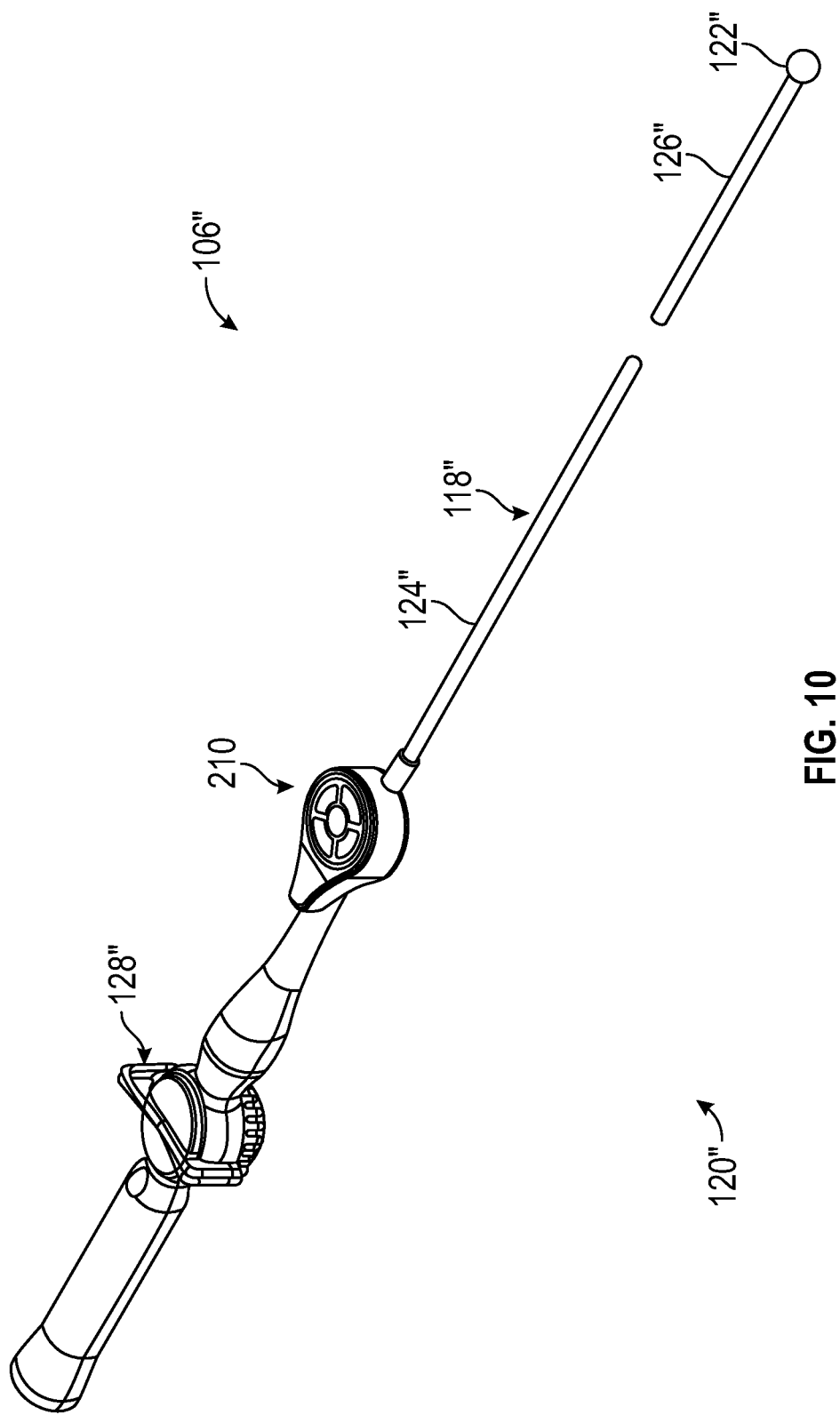
FIG. 10 is an isometric view of the catheter and the second input device of FIG. 9.
Figure 11:
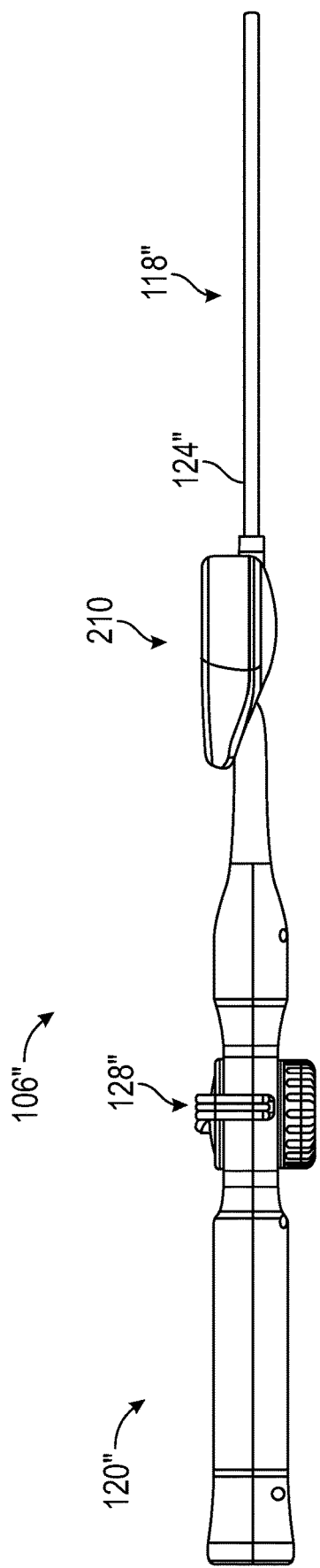
FIG. 11 is a side view of the second input device and a portion of the catheter of FIG. 9.
Figure 12:
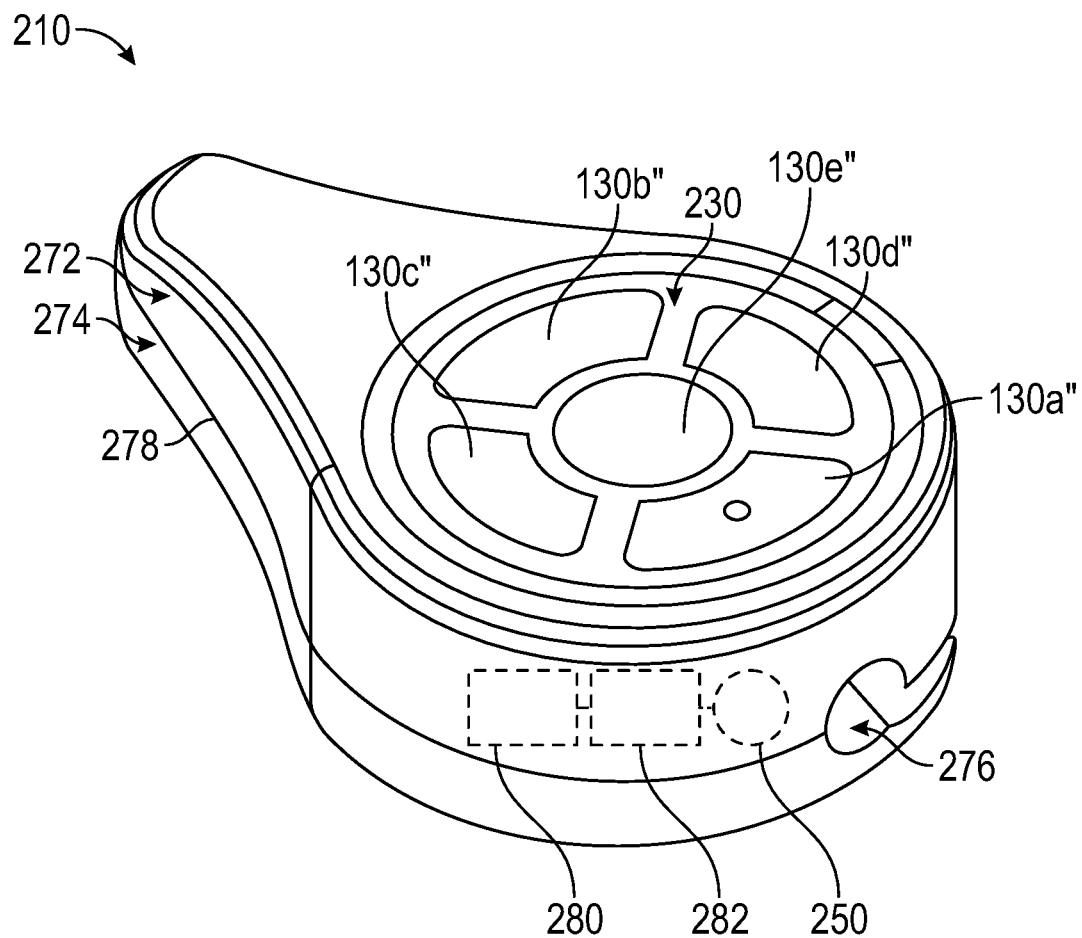
FIG. 12 is an isometric view of the second input device of FIG. 9.

As another example, while the second input device has been described as being disposed along the handle of the catheter or as separate from the catheter, other implementations are additionally or alternatively possible. For example, referring now to FIGS. 9-12, a system 100" can include a second input device 210 securable to a catheter shaft 118" of a catheter 106". For the sake of efficient and clear description, elements designated by double prime (") element numbers in FIGS. 9-12 should be understood to be analogous to elements with unprimed and/or primed element numbers described herein, unless otherwise indicated or separately made clear from context, and, thus, are not described separately from primed or unprimed counterparts, except to highlight certain aspects. Thus, for example, element number 106" in FIG. 9 should be understood to be a catheter analogous to the catheter 106 (FIGS. 1 and 4) and the catheter 106' (FIG. 8), and element number 118" in FIG. 9 should be understood to be a catheter shaft analogous to the catheter shaft 118 (FIGS. 1 and 4) and the catheter shaft 118' (FIG. 8), unless otherwise indicated or made clear from the context.

The second input device 210 can be in communication (e.g., wireless communication) with the catheter interface unit 104" to transmit navigation commands and/or input commands to a second portion of the graphical user interface 116" according to any of the various different methods described herein. As described in greater detail below, securing the second input device 210 to the catheter shaft 118" of the catheter 106" can facilitate locating the second input device 210 by the physician without requiring the physician to divert his or her attention from the medical procedure. Additionally, or alternatively, as also described in greater detail below, securing the second input device 210 to the catheter shaft 118" can facilitate single-handed operation of the second input device 210 during a medical procedure.

In general, the second input device 210 can include a user interface 230, a wireless transmitter 250, and a housing 270 carrying the user interface 230 and the wireless transmitter 250. The user interface 230 can include one or more inputs 130a", 130b", 130c", 130d", and 130e", which can be any one or more of the various different inputs described herein. In use, the physician can depress or otherwise engage the one or more inputs 130a", 130b", 130c", 130d", and 130e", and the wireless transmitter 250 can be in communication with the user interface 230 to send one or more navigation and/or control commands to a remote processor, such as the processing unit 112", according to any one or more of the various different methods described herein. Thus, for example, the physician can manipulate the user interface 230 to send one or more navigation and/or control commands to the processing unit 112" based on input options displayed on a portion of a graphical user interface, such as the graphical user interface 116", according to any of the various different methods described herein.

The second input device 210 can be at least one of electrically and fluidically isolated from a handle 120" and the catheter shaft 118" to facilitate, for example, robust operation of the second input device 210 throughout the medical procedure, independent of the catheter 106". For example, the housing 270 can define a volume, and the wireless transmitter 250 can be disposed within the volume defined by the housing 270. The one or more inputs 130a", 130b", 130c", 130d", and 130e" can be at least partially disposed outside of the volume defined by the housing 270 such that the one or more inputs 130a", 130b", 130c", 130d", 130e" form at least a portion of an outer surface of the second input device 210 and are accessible by the physician. In certain instances, the volume defined by the housing 270 can be substantially resistant to fluid ingress such that the wireless transmitter 250 is protected from fluid that may contact the second input device 210 during a medical procedure. Additionally, or alternatively, the one or more inputs 130a", 130b", 130c", 130d", 130e" can be arranged relative to the housing 270 to reduce the likelihood of fluid ingress into the volume defined by the housing 270.

In certain implementations, the housing 270 can be securable to an outer circumference of the catheter shaft 118" with the user interface 230 partially constrained in at least one direction relative to the catheter shaft 118". Such constrained movement of the user interface 230 relative to the catheter shaft 118" can, for example, facilitate locating the user interface 230 by the physician during a medical procedure. That is, given that the user interface 230 is at least partially constrained in at least one direction relative to the catheter shaft 118", the physician can find the user interface 230 by moving his or her hand along the catheter shaft 118" to find the user interface 230. Thus, the catheter shaft 118" itself can act as a guide for the physician, which can reduce the need for the physician to divert his or her attention away from the graphical user interface 116" to find the user interface 230 of the second input device 210.

As an example, with the housing 270 secured to the outer circumference of the catheter shaft 118", the user interface 230 can be at least partially constrained in a radial direction relative to the catheter shaft 118". As used herein, partial constraint in the radial direction can include movement of less than about 2 cm (e.g., less than about 1 cm) and, therefore, can include complete constraint in the radial direction. In certain implementations, the user interface 230 can be movable along an axis defined by the catheter shaft 118" and, thus, partial constraint in the radial direction can include radial movement sufficient to allow the housing 270 and the user interface 230 to move along the axis defined by the catheter shaft 118". It should be appreciated that, in such implementations in which the housing 270 and the user interface 230 are movable along the axis defined by the catheter shaft 118", the housing 270 and the user interface 230 can be movable between the handle 120" of the catheter 106" and a sheath at the insertion site of the catheter 106" into the patient.

Additionally, or alternatively, the housing 270 can be securable in a fixed axial position relative to the catheter shaft 118". For example, an interference fit between the outer circumference of the catheter shaft 118" and the housing 270 can hold the housing 270 in a fixed axial position relative to the catheter 118" during a medical procedure. The fixed axial position can be any of various different axial positions along the catheter shaft 118". For example, the housing 270 can be secured to a proximal end region 124" of the catheter shaft 118" with the housing 270 extending distal to the handle 120" of the catheter 106". Additionally, or alternatively, the housing 270 can be secured to the proximal end region 124 of the catheter shaft 118" such that the housing 270 is adjacent to the handle 120".

With the housing 270 at least partially constrained in at least one direction relative to the catheter shaft 118", the user interface 230 can be rotatable about the catheter shaft 118" and, optionally, rotatable about the handle 120" coupled to the catheter shaft 118". For example, the user interface 230 can be rotatable about an axis of rotation coaxial with an axis defined by the catheter shaft 118" (e.g., freely rotatable 360 degrees about the axis of rotation such that the user interface 230 is rotatable through multiple revolutions about the axis of rotation). Rotation of this type can facilitate, for example, single-handed operation of the second input device 210 by the physician. That is, the physician can rotate the user interface 230 as necessary to align the user interface 230 in a desired radial orientation.

The housing 270 can be at least partially formed of a material compatible with sterilization (e.g., any of the various different sterilization techniques described herein) and, in some instances, the housing 270 can be sterilized prior to being secured to the catheter shaft 118". Additionally, or alternatively, the second input device 210 can include a cover enclosing the housing 270 and the user interface 230, and the cover can be formed of a material compatible with sterilization such as any of the various sterilization techniques described herein. A cover separable from the housing 270 can be useful, for example, in implementations in which the housing 270 carries one or more components (e.g., batteries) that are not readily compatible with sterilization. In such instances, the cover can be sterilized apart from the second input device 210 and then used to cover the second input device 210 prior to securing the second input device 210 to the catheter shaft 118".

In general, the housing 270 can be securable to the catheter shaft 118" without the use of tools. The ability to secure the housing 270 to the catheter shaft 118" in this way can for example, facilitate securing the housing 270 to the catheter shaft 118" by the physician or other medical personnel in the sterile field.

As an example, the housing 270 can include a first section 272 and a second section 274, each defining a portion (e.g., substantially half) of a recess 276. The first section 272 and the second section 274 can be releasably engageable with one another to position the recess 276 about at least a portion of an outer circumference of the catheter shaft 118". The releasable engagement between the first section 272 and the second section 274 can be achieved through an interference fit between mating features of the first section 272 and the second section 274. Further, or instead, the first section 272 can include a first material and the second section 274 can include a second material magnetically attracted to the first material such that placing the first section 272 and the second section 274 in proximity to one another results in coupling the first section 272 to the second section 274 through the magnetic force between the first material and the second material.

In certain instances, the first section 272 and the second section 274 can be coupled to one another at a hinge 278 pivotable to move the first section 272 and the second section 274 in a clamshell arrangement into engagement with each other to position the recess 276 about the catheter shaft 118". The hinge 278 can be useful, for example, for accounting for manufacturing tolerances associated with the outer circumference of the catheter shaft 118". Additionally, or alternatively, the hinge 278 can be useful for reducing the number of parts needed to be manipulated by the physician or other medical personnel in the sterile field to secure the second input device 210 to the catheter shaft 118".

As an additional, or alternative, example, the housing 270 can include a clip defining the recess 276 and positionable about at least a portion of the outer circumference of the catheter shaft 118". For example, the clip may be "U-shaped" such that the recess 276 is defined by legs that are movable away from one another to accept the catheter shaft 118" and biased back toward one another to hold the second input device 210 about the outer circumference of the catheter shaft 118".

The recess 276 can be sized, for example, to fit about a standard catheter size such that the second input device 210 can be securable to any of various different catheters of a given standard catheter size, including catheters made by different manufacturers. Additionally, or alternatively, the recess 276 can be sized to account for manufacturing tolerances associated with a given standard catheter size.

With the housing 270 secured to the outer circumference of the catheter shaft 118", the user interface 230 can be suitable for single-handed operation by the physician during a medical procedure. Such single-handed operation can facilitate, for example, simultaneous or substantially simultaneous operation of the user interface 230 with one hand while the physician holds the catheter shaft 118" or the handle 120" with the other hand. Additionally, or alternatively, the remote communication device 210 can be secured to the outer circumference of the catheter shaft 118" at a position distal to an articulation controller 128" of the catheter 106". The articulation controller 128" can be, for example, any of the various different articulation controllers described herein to modify a distal end region 126" of the catheter shaft 118". In certain implementations, the physician can operate the articulation controller 128" with one hand while simultaneously or substantially simultaneously operating the user interface 230 with the other hand.

In general, with the housing 270 secured to the outer circumference of the catheter shaft 118", the one or more inputs 130a", 130b", 130c", 130d", 130e" can be arranged relative to the catheter shaft 118" such that manipulation of the one or more inputs 130a", 130b", 130c", 130d", 130e" does not cause unintended movement of the housing 270 relative to the catheter shaft 118". For example, the one or more inputs 130a", 130b", 130c", 130d", 130e" of the user interface 230 can be any of the various different inputs described herein and can be depressible or otherwise engageable in a direction parallel to the at least one partially constrained direction of the user interface 230 such that the constrained movement of the user interface 230 can counter the force exerted on the one or more inputs 130a", 130b", 130c", 130d", and 130e" and, thus, restricts undesired movement of the second input device 210 as one or more inputs are received. Additionally, or alternatively, in implementations in which the user interface 230 is rotatable about an axis defined by the catheter shaft 118", the one or more inputs 130a", 130b", 130c", 130d", 130e" can be depressible in a direction transverse to the axis of rotation of the user interface 230 such that providing an input is less likely to result in inadvertent rotation of the user interface 230 about the catheter shaft 118". It should be appreciated from these examples that such an arrangement of forces can facilitate single-handed operation of the second input device 210. That is, the physician can use a single hand to depress the one or more inputs 130a", 130b", 130c", 130d", 130e" without requiring the use of a second hand to hold the user interface 230 in place as input is provided at the one or more inputs 130a", 130b", 130c, 130d", 130e".

In certain implementations, the second input device 210 can further include a power source 280 carried by the housing 270 and in electrical communication with the wireless transmitter 250 to power the wireless transmitter 250. The power source 280 can be for example one or more batteries. Additionally, or alternatively, the power source 280 can be releasably coupled to the housing to facilitate replacement or recharging of the power source 280 (e.g., during or in between medical procedures).

In some implementations, the second input device 210 can further include a processor 282 in communication with the user interface 230 and the wireless transmitter 250. For example, the processor 282 can receive a signal from the one or more inputs 130a", 130b", 130c", 130d", 130e" and send a corresponding signal to the wireless transmitter 250 for transmission. In addition to, or instead of, the processor 282, the second input device 210 can include circuitry to receive a signal from the one or more inputs 130a'', 130b'', 130c'', 130d'', 130e'' and send a corresponding signal to the wireless transmitter 250.

While second input devices have been described as including housings that can be clamped onto a shaft of a catheter, other implementations are additionally or alternatively possible. For example, a second input device can include a housing through which a distal end region of a catheter can be moved. Through such movement of the distal end region of the catheter through the housing, the second device can be disposed about a shaft of the catheter. Thus, in certain implementations, the distal end region of the catheter can be introduced into a patient through the housing of the second input device. For example, the housing of the second input device can include an introducer sheath positionable, as is known in the art, in vasculature of the patient and through which the distal end region of the catheter can be introduced into the vasculature of the patient during a procedure. Additionally, or alternatively, the housing of the second input device can include an insertion sleeve positionable relative to the introducer sheath, as is also known in the art. In use, the distal end region of the catheter can be moved through the insertion sleeve and into vasculature of the patient via an introducer sheath positioned in the vasculature of the patient.

While second input devices have been described as being hand operated, other implementations are additionally or alternatively possible. For example, a second input device can include a foot pedal operable by the physician tapping one or more inputs on the foot pedal to navigate through a second portion of a graphical user interface according to one or more of the methods described herein.

While second input devices have been described as being physical devices manipulated by the physician, other implementations are additionally or alternatively possible. For example, a second input device can be implemented through a virtual reality system (such as Leap Motion available from Leap Motion, Inc. of San Francisco, Calif.). In such an implementation, a physician's hand or hands can interact with a virtual reality environment to navigate and provide inputs to the second portion of the graphical user interface according to any one or more of the methods described herein.

While second input devices have been described as being operated with one or more of a physician's limbs, other implementations are additionally or alternatively possible. For example, the second input device can be responsive to one or more voice commands (e.g., "up," "down," "right," "left," and "enter") to navigate and provide inputs to the second portion of the graphical user interface according to any one or more of the methods described herein. Such a second input device responsive to voice commands can, for example, reduce the need for separate hardware in the sterile field with the physician.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals.

It will further be appreciated that a realization of the processes or devices described above may include computer-executable code created using a structured programming language such as C, an object oriented programming language such as C++, or any other high-level or low level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices.

In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. A method comprising:
   receiving a signal indicative of a location of a cardiac catheter in a cavity of a patient's heart;
   simultaneously displaying—
   (i) a graphical representation of the cavity of the patient's heart on a first portion of a graphical user interface, wherein the graphical representation is based on the received location signal from the cardiac catheter,
   (ii) a first set of a plurality of input options associated with only a first input device on the first portion of the graphical user interface, and
   (iii) a second set of a plurality of input options on a second portion of the graphical user interface separate from the first portion,
   wherein the second set of the plurality of input options is associated with a second input device different than the first input device, and wherein the second set of the plurality of input options represented on the second portion of the graphical user interface corresponds to a current state of a state machine having a plurality of states;
   receiving, from the first input device, a first input command based on the first set of the plurality of input options;
   receiving, from the second input device, a second input command based on the second set of the plurality of input options; and
   based on the first input command and the second input command, modifying the graphical representation in the first portion of the graphical user interface.

2. The method of claim 1, wherein modifying the graphical representation includes adjusting the displayed graphical representation according to an order in which the first input command and the second input command are received.

3. The method of claim 1, wherein at least some of the second set of the plurality of input options are the same as some of the first set of the plurality of input options.

4. The method of claim 1, wherein receiving the first input command includes receiving the first input command along a first communication channel and receiving the second input command includes receiving the second input command along a second communication channel, each communication channel dedicated to the respective portion of the graphical user interface.

5. The method of claim 1, further comprising receiving navigation commands for moving, within the second portion of the graphical user interface, between the options in the second set of the plurality of input options.

6. The method of claim 1, wherein the second input command or at least one of the navigation commands changes a current state of a state machine.

7. The method of claim 5, wherein the navigation commands include discrete direction commands.

8. The method of claim 7, wherein the discrete direction commands include commands for left, right, up, and down navigation in the second portion of the graphical user interface.

9. The method of claim 5, further comprising detecting receipt of an initial command, the initial command being one of the second input command or one of the navigation commands, and, based on the detected receipt of the initial command, changing one or more display features of the second portion of the graphical user interface.

10. The method of claim 9, wherein the changing one or more display features of the second portion of the graphical user interface includes changing the one or more display features of the second portion, relative to the first portion of the graphical user interface, between a baseline configuration and modified configuration.

11. The method of claim 10, wherein changing the one or more display features of the second portion of the graphical user interface relative to the first portion of the graphical user interface between a baseline configuration and a modified configuration includes changing a size of the second portion of the graphical user interface relative to a size of the first portion of the graphical user interface.

12. The method of claim 1, wherein the first portion is viewable on the graphical user interface at the same time that the second portion is viewable on the graphical user interface.

13. The method of claim 12, wherein modification of the displayed graphical representation includes adjusting an orientation of a displayed view of the graphical representation of the heart cavity of the patient.

14. The method of claim 1, wherein receiving the second input command includes receiving a wireless input command.

15. The method of claim 1, wherein the second input device is a remote device and receiving the second input command includes receiving an input command from the remote device.

16. A non-transitory, computer-readable storage medium storing instructions that, when executed by a computing system, cause the computing system to perform operations comprising:
   receiving a signal indicative of a location of a catheter tip in a cavity of a patient's heart;
   simultaneously displaying, on a graphical user interface, (i) a graphical representation of the catheter tip in the patient's heart, (ii) a first set of a plurality of input options associated with only a first input device, and (iii) a second set of a plurality of input options associated with a second input device different than the first input device, wherein the second set of the plurality of input options represented on the second portion of the graphical user interface corresponds to a current state of a state machine having a plurality of states;
   receiving, from the first input device, a first input command responsive to the first set of the plurality of input options;
   receiving, from the second input device, navigation commands and a second input command, the navigation commands for moving through the second set of the plurality of input options, and the second input command responsive to the second set of the plurality of input options; and
   based on the first input command and the second input command, modifying the graphical representation on the graphical user interface.

17. The storage medium of claim 16, wherein the operations further comprise displaying the first set of the plurality of input options on a first portion of the graphical user interface, and displaying the second set of the plurality of input options on a second portion of the graphical user interface.

18. The storage medium of claim 16, wherein receiving the navigation commands includes receiving an analog command for navigating through the second set of the plurality of input options.

19. The storage medium of claim 16, the operations further comprising modifying, based on the received navigation commands, one or more display features of the second set of the plurality of input options between a baseline configuration and a modified configuration.

\* \* \* \* \*